(12) United States Patent
Buolamwini

(10) Patent No.: US 8,927,570 B2
(45) Date of Patent: *Jan. 6, 2015

(54) 1-NAPHTHYL-OR 1-DIHYDROACENAPHTHENYL-PYRIDO [B]INDOLES AND USES THEREOF IN TREATING CANCERS

(71) Applicant: John K. Buolamwini, Cordova, TN (US)

(72) Inventor: John K. Buolamwini, Cordova, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/664,089

(22) Filed: Oct. 30, 2012

(65) Prior Publication Data

US 2013/0131070 A1    May 23, 2013

Related U.S. Application Data

(63) Continuation-in-part of application No. 12/799,485, filed on Apr. 26, 2010, now Pat. No. 8,329,723.

(60) Provisional application No. 61/214,582, filed on Apr. 24, 2009.

(51) Int. Cl.
    A61K 31/437    (2006.01)
    C07D 471/14    (2006.01)
    C07D 495/04    (2006.01)
    A61K 45/06     (2006.01)
    C07D 471/04    (2006.01)
    C07D 491/048   (2006.01)

(52) U.S. Cl.
    CPC ............ *C07D 471/04* (2013.01); *C07D 495/04* (2013.01); *A61K 45/06* (2013.01); *A61K 31/437* (2013.01); *C07D 491/048* (2013.01)
    USPC ........................................... 514/292; 546/85

(58) Field of Classification Search
    CPC ............................ A61K 31/437; C07D 471/14
    USPC .............................................. 514/292; 543/85
    See application file for complete search history.

(56) References Cited

PUBLICATIONS

Ho, et al. Canadian Journal of Chemistry, 45(23), 1967, 2963-2967.*

* cited by examiner

*Primary Examiner* — Douglas M Willis
(74) *Attorney, Agent, or Firm* — Benjamin Aaron Adler

(57) ABSTRACT

Provided are 1-aryl or 1-heteroaryl substituted beta-carboline compounds or indole analogs thereof having the structure:

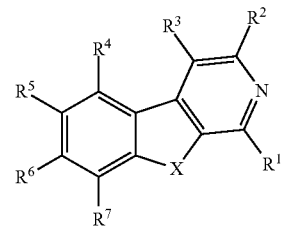

where X is NH, N—$C_1$-$C_4$ alkyl, S, or O; $R^1$ is 1-naphthyl or 1-dihydroacenaphthenyl, each optionally substituted with a halogen; and $R^2$, $R^3$, $R^4$, $R^5$, $R^6$, and $R^7$ are independently H H, OH, halogen, CN, $C_1$-$C_4$ alkyl, $C_1$-$C_4$ alkoxy, $C_1$-$C_4$ haloalkoxy, —C(O)O$C_1$-$C_4$ ester, —$C_1$-$C_4$—$SO_2$—NH—$C_1$-$C_4$ sulfonamide, or phenyl with the proviso that X is NH, $R^1$ is 1-naphthyl or 1-naphthyl substituted with a halogen and one of $R^5$, $R^6$, or $R^7$ is $C_1$-$C_4$ alkoxy, then $R^2$, $R^3$, $R^4$, $R^5$, $R^6$, and $R^7$ are independently H, OH, halogen, CN, $C_1$-$C_4$ haloalkoxy, —C(O)O$C_1$-$C_4$ ester, —$C_1$-$C_4$—$SO_2$—NH—$C_1$-$C_4$ sulfonamide, or phenyl such that at least two of $R^2$, $R^3$, $R^4$, $R^5$, $R^6$, and $R^7$ are other than H. Also provided are methods for inhibiting proliferation of cells associated with a cell proliferative disease by contacting the cell with the compounds provided herein.

13 Claims, 12 Drawing Sheets a = THF, 0°C-rt; b = Pd-C, xylene, reflux; c = Pd/C/K-10, MW, 150°C $R^1$ = 1-naphthyl, $R^2$ = $OCH_3$, $CH_3$, $CH_2SO2NHCH_3$, $OCF_3$

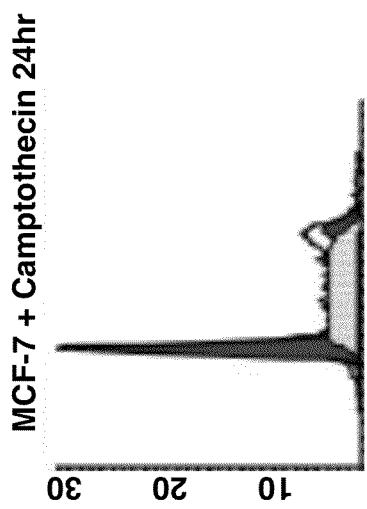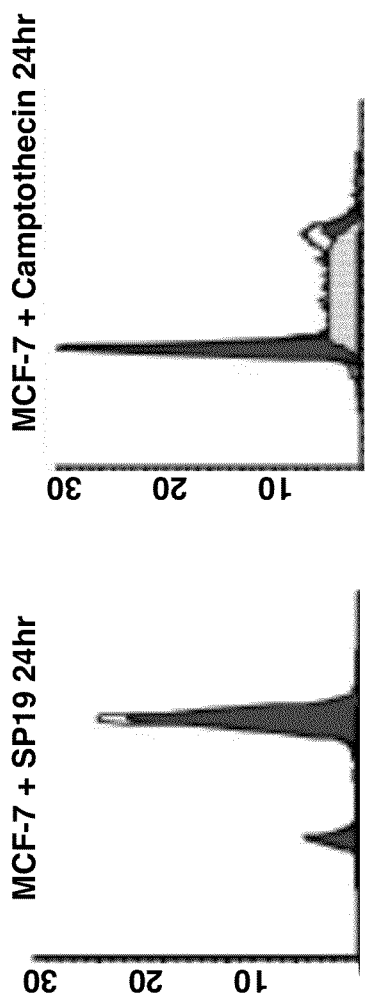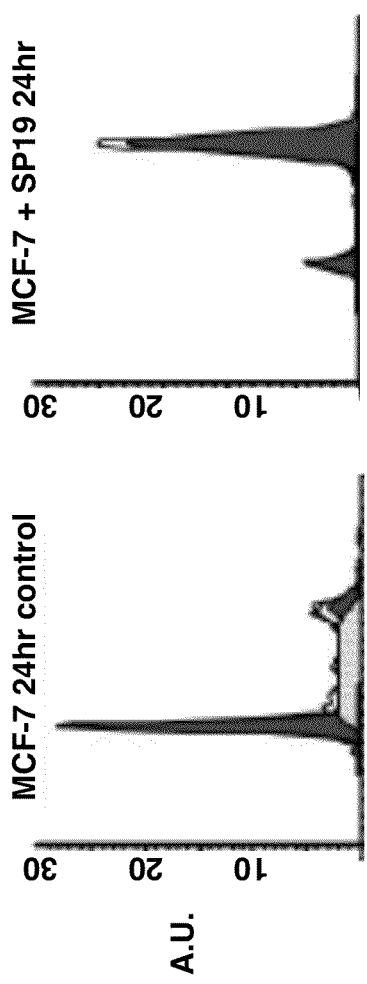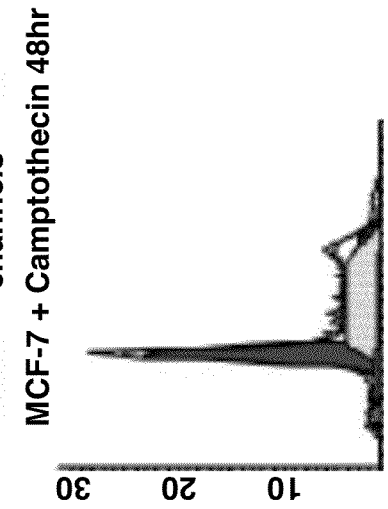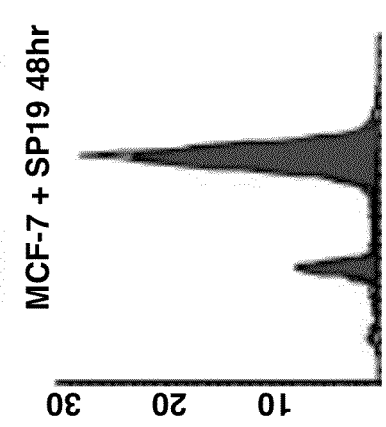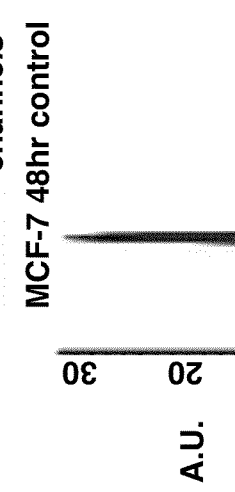

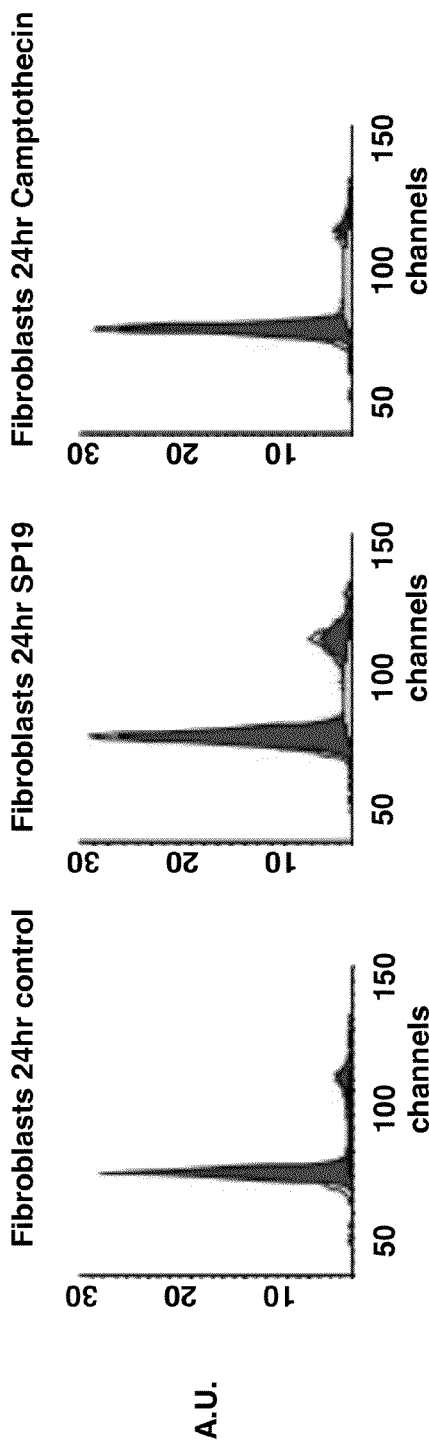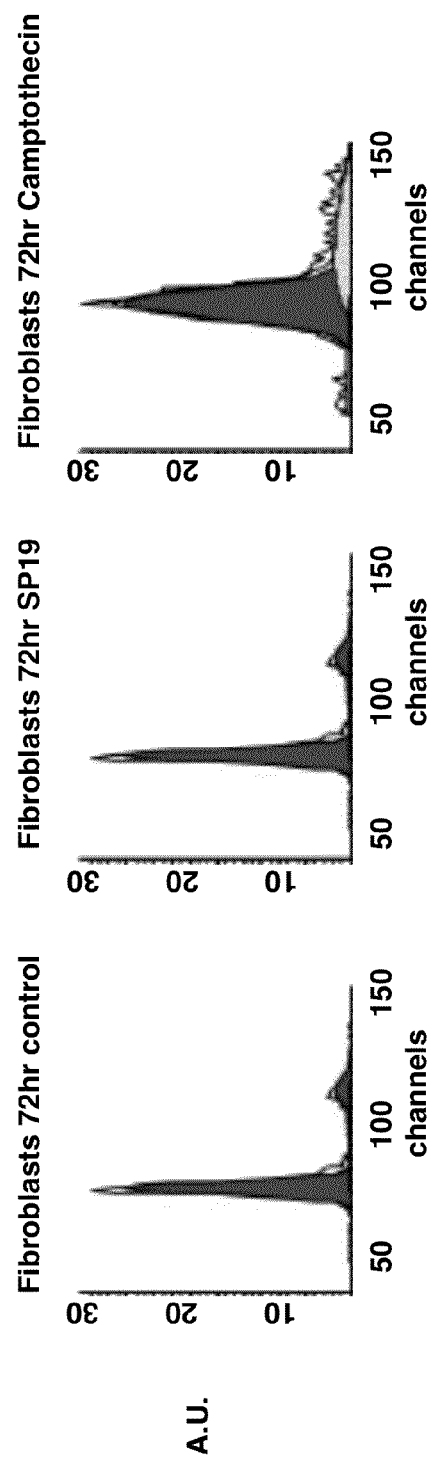

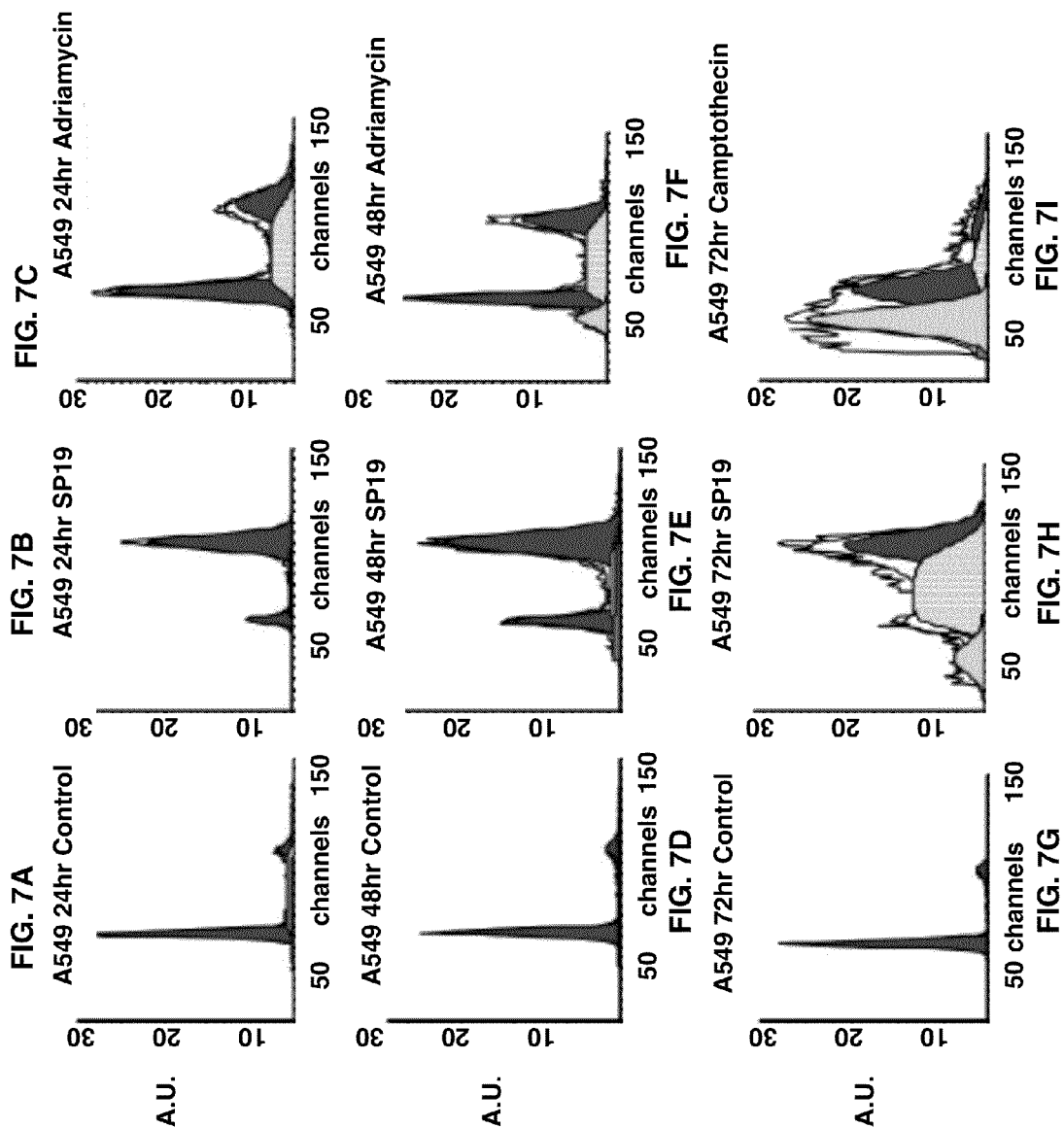

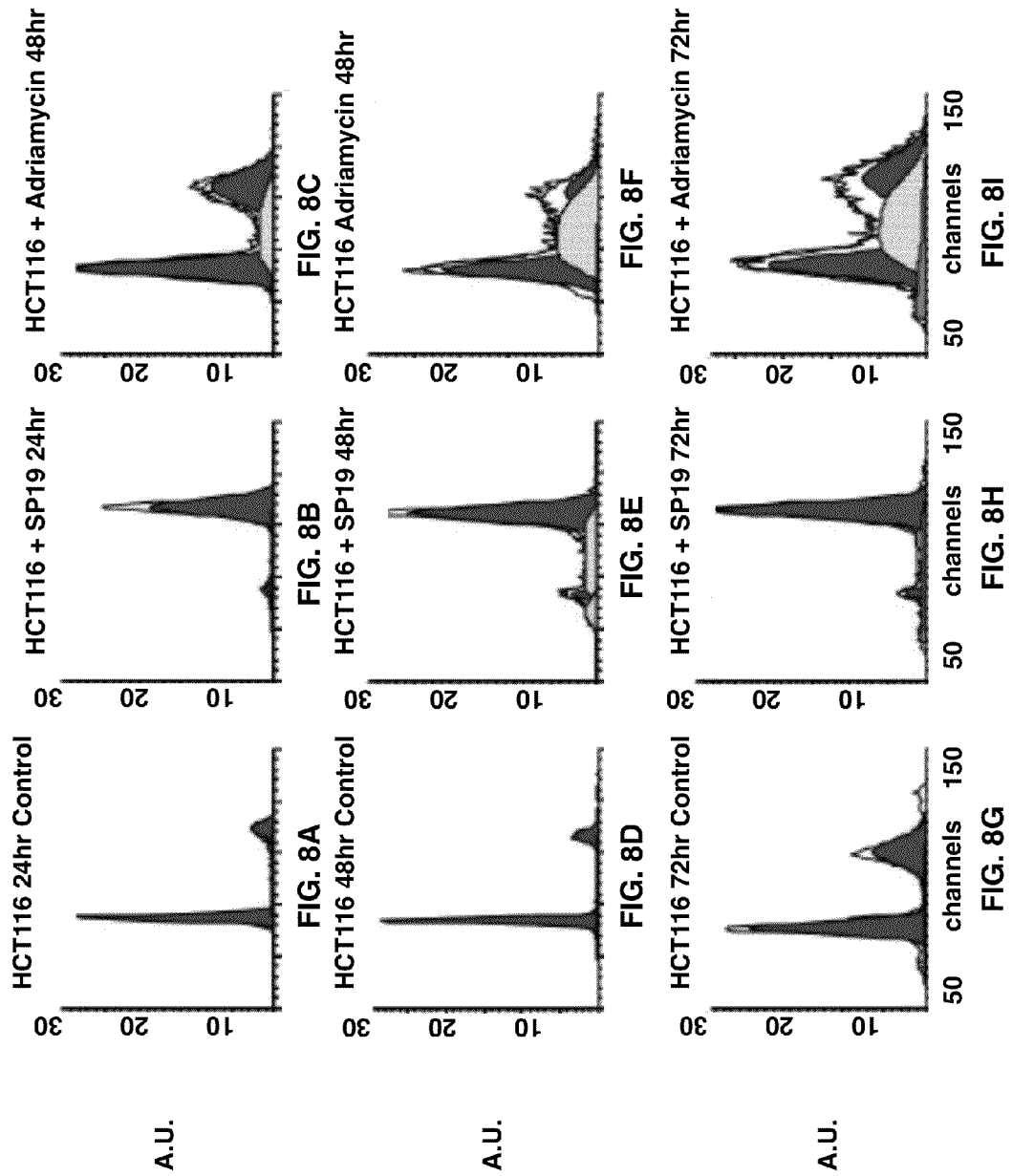

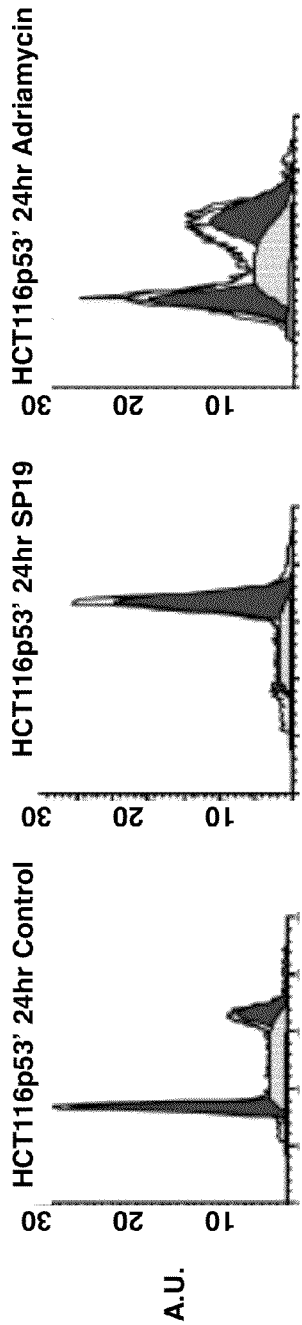
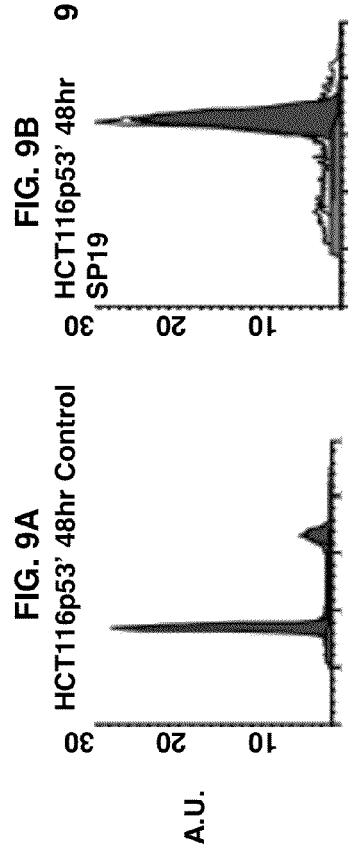
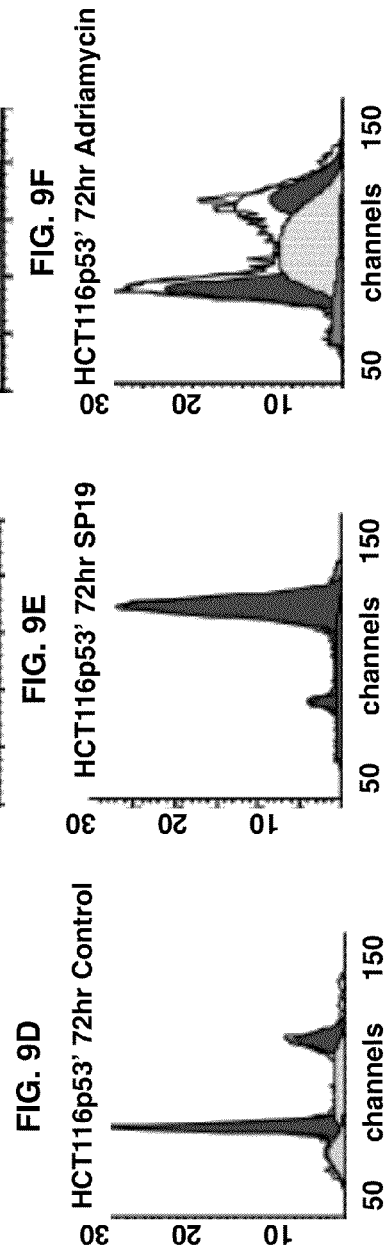

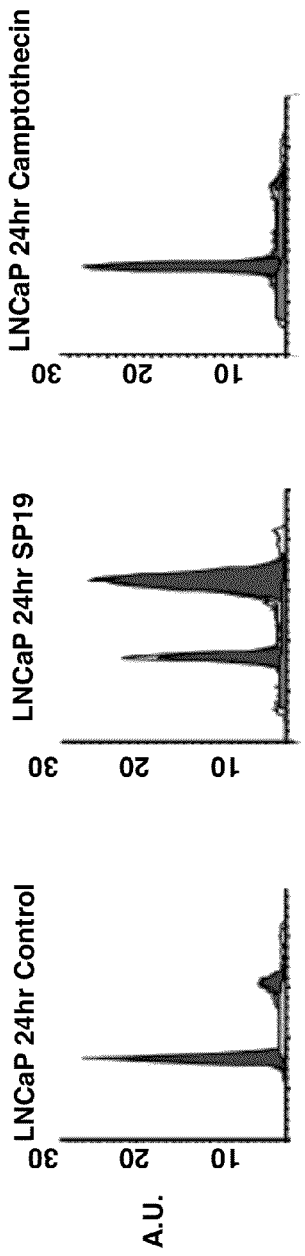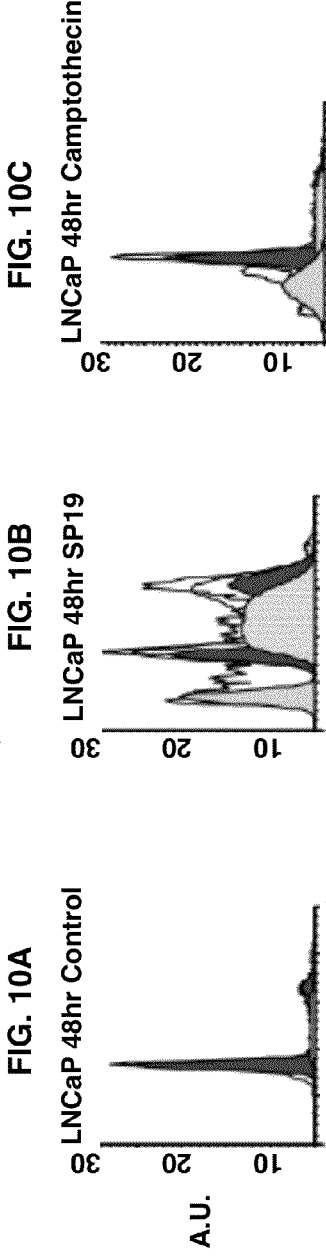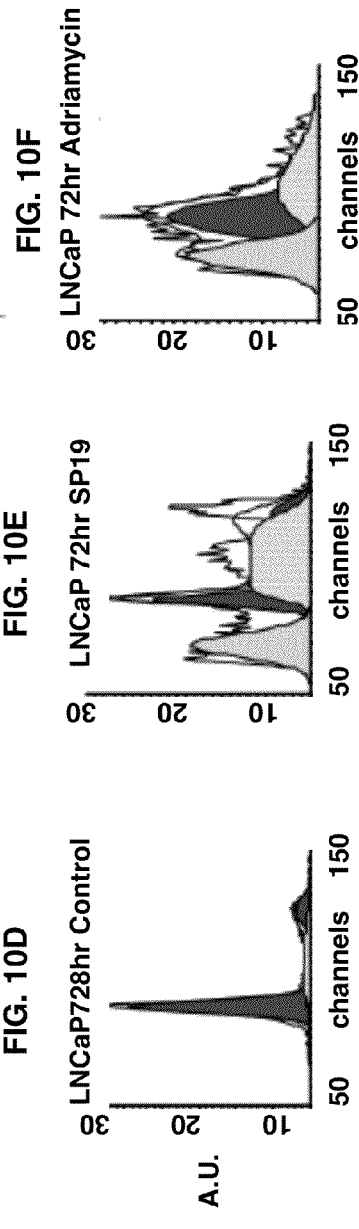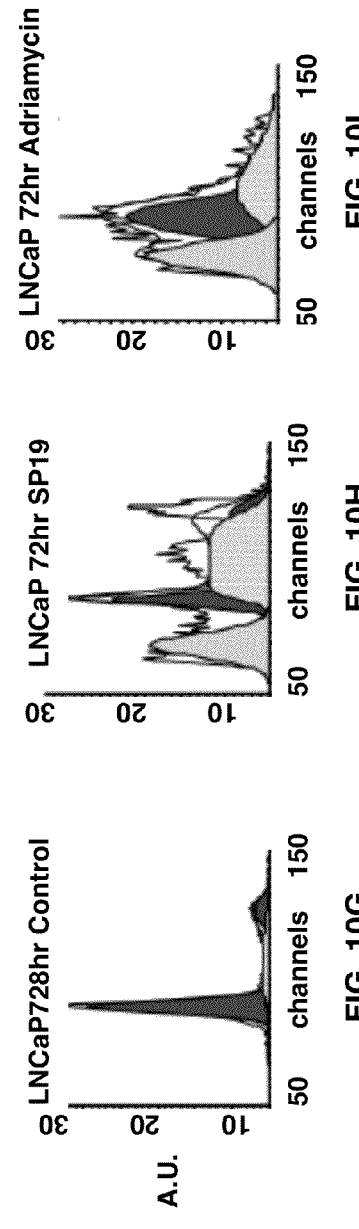

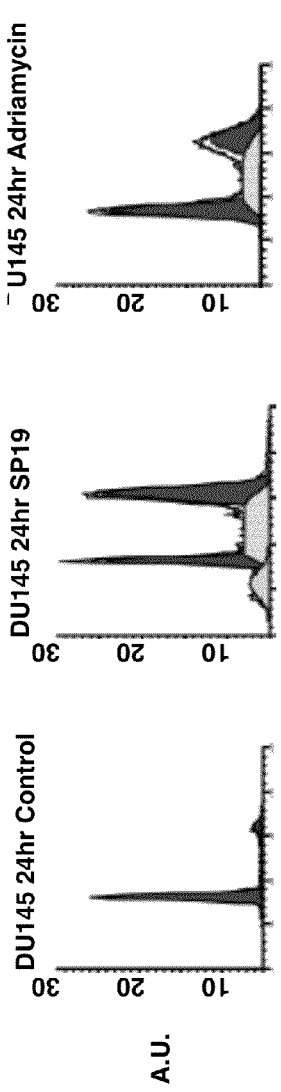
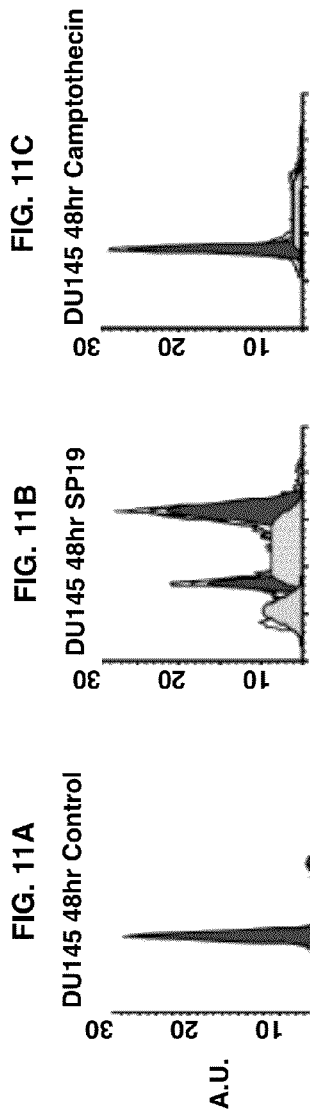
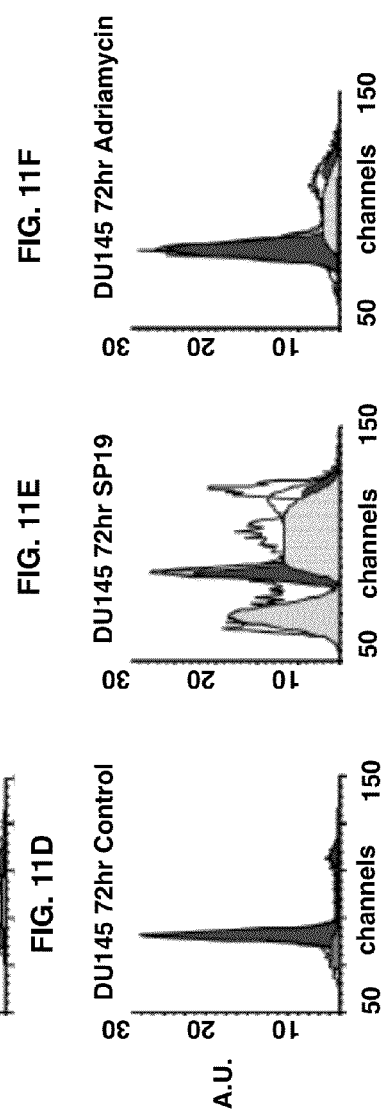

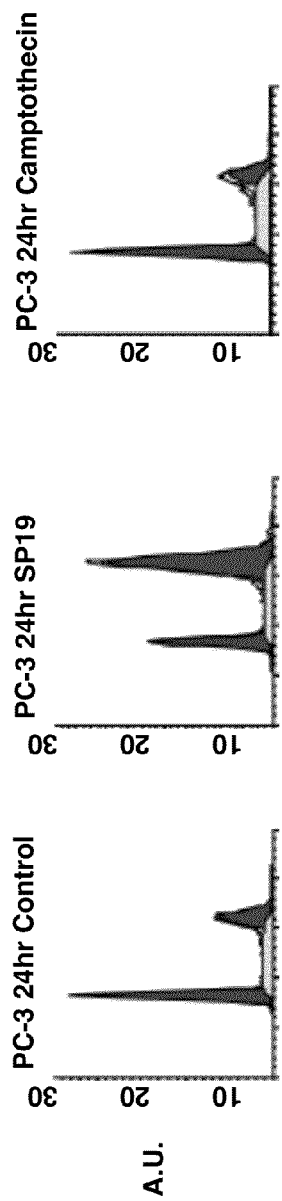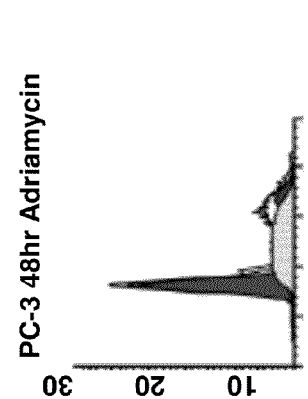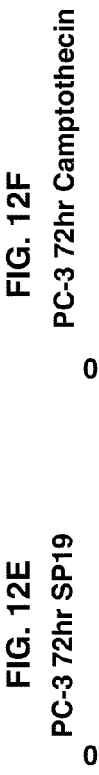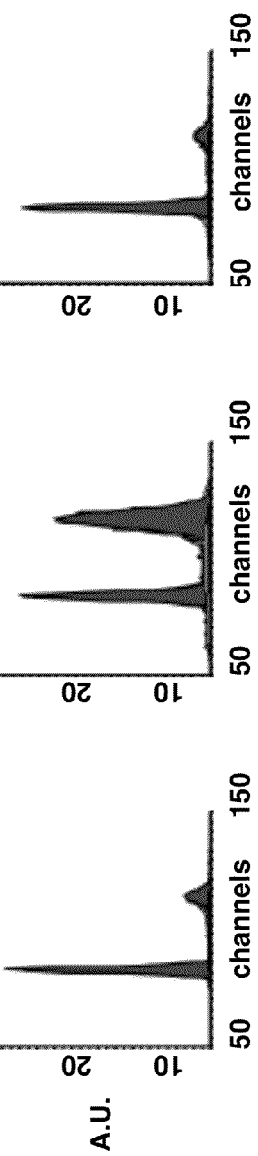

1-NAPHTHYL-OR 1-DIHYDROACENAPHTHENYL-PYRIDO[B] INDOLES AND USES THEREOF IN TREATING CANCERS

CROSS-REFERENCE TO RELATED APPLICATIONS

This continuation-in-part application claims benefit of priority under 35 U.S.C. §120 of pending non-provisional application U.S. Ser. No. 12/799,485, filed Apr. 26, 2010, which claims benefit of priority under 35 U.S.C. §119(e) of provisional application U.S. Ser. No. 61/214,582, filed Apr. 24, 2009, now abandoned, the entirety of both of which is hereby incorporated by reference.

FEDERAL FUNDING LEGEND

This invention was made with government support under Grant Number R15CA100102 awarded by the National Institutes of Health—National Cancer Institute. The government has certain rights in invention.

BACKGROUND OF THE INVENTION

1. Field of the Invention

The present invention relates to the fields of organic chemistry and chemotherapeutic compounds. Specifically, the present invention relates to 1-aryl(heteroaryl)pyrido[b]indoles or indole analogs thereof and their uses in treating cancers.

2. Description of the Related Art

More than half a million people die of cancer every year in the United States, making cancer the second leading cause of death in this country after heart disease. The total economic cost of cancer to the United States has been estimated at over $263 billion. Thus, the need for effective cancer therapies cannot be overstated.

The β-carboline scaffold and reduced derivatives thereof appear to be 'privileged' bioactive structures that occur in a variety of natural products with anticancer activity among other effects (1). For example, the ability of harmine to affect cyclin-dependent kinases and cancer cell proliferation has been described (2). Also, have reported a structure-activity relationship of tetrahydro-β-carbolines as cell cycle arresting agents and inducers of apoptosis has been reported (3). Tangutorine, a β-carboline alkaloid, was recently shown to be an inducer of p21 expression and abnormal mitosis in human colon cancer cells (4). Isostrychnopentam119(eine, an indolomonoterpenic alkaloid containing a tetrahydro-β-carboline moiety induces cell cycle arrest and apoptosis in human colon cancer cells (5).

There is still, however, a recognized need in the art for improved chemotherapeutics and cancer therapies. Specifically, the prior art is deficient in 1-aryl- or 1-heteroarylpyrido[b]indoles, for example substituted β-carbolines effective to inhibit cancer cell proliferation. The present invention fulfills this long standing need in the art.

SUMMARY OF THE INVENTION

The present invention is directed to a β-carboline compound having the structure

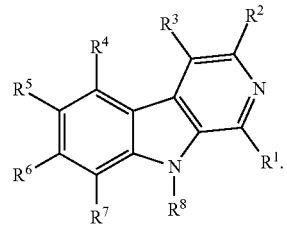

The $R^1$ substituents are phenyl, furanyl, naphthyl, anthracyl, phenanthracyl, quinolinyl, isoquinolinyl, quinoxalinyl, or phenyl substituted with pyridinyl, or $C_1$-$C_4$ alkyl or $C_{1-4}$ alkoxy derivatives thereof. The $R^2$-$R^8$ substituents may be independently, hydrogen, $C_{1-4}$ alkyl, $C_{1-4}$ alkoxy, $C_{1-4}$ alkoxyphenyl, halogen, thiol, alkylthiol, sulfonyl, sulfonamide, amide, substituted amide, ester, nitrile, amino, substituted amine, haloalkyl, haloalkoxy, or acyl.

The present invention also is directed to a substituted β-carboline compound having the structure

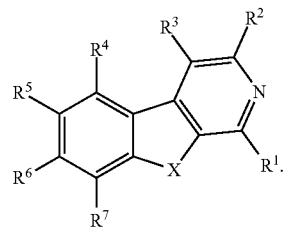

The X heteroatom is NH, N—$C_1$-$C_4$ alkyl, S, or O. The $R^1$ substituents are furanyl, 1-naphthyl, 1-dihydroacenaphthenyl, anthracyl, phenanthracyl, 3-quinolinyl, 5-quinolinyl, isoquinolinyl, quinoxalinyl, phenyl substituted with pyridinyl each optionally substituted with a halogen, $C_1$-$C_4$ alkyl, or $C_1$-$C_4$ alkoxy. The $R^2$-$R^7$ substituents are independently H, OH, halogen, CN, $C_1$-$C_4$ alkyl, $C_1$-$C_4$ alkoxy, $C_1$-$C_4$ haloalkyl, $C_1$-$C_4$ haloalkoxy, —C(O)O$C_1$-$C_4$ ester, —$C_1$-$C_4$—$SO_2$—NH—$C_1$-$C_4$ sulfonamide, phenyl, $C_1$-$C_4$ alkoxyphenyl with the proviso that, when X is NH, at least one of $R^2$, $R^3$, $R^4$, $R^5$, $R^6$, and $R^7$ is other than H.

The present invention is directed to a related substituted β-carboline compound having the structure where the X heteroatom is as described supra. The $R^1$ substituents are 1-naphthyl or 1-dihydroacenaphthenyl each optionally substituted with Br or F. The $R^2$-$R^7$ substituents are independently H, OH, halogen, CN, $C_1$-$C_4$ alkyl, $C_1$-$C_4$ alkoxy, $C_1$-$C_4$ haloalkoxy, —C(O)O$C_1$-$C_4$ ester, —$C_1$-$C_4$—$SO_2$—NH—$C_1$-$C_4$ sulfonamide, or phenyl with the proviso that when X is NH, $R^1$ is 1-naphthyl or 1-naphthyl substituted with a halogen and one of $R^5$, $R^6$, or $R^7$ is $C_1$-$C_4$ alkoxy, then $R^2$, $R^3$, $R^4$, $R^5$, $R^6$, and $R^7$ are independently H, OH, halogen, CN, $C_1$-$C_4$ haloalkoxy, —C(O)O$C_1$-$C_4$ ester, —$C_1$-$C_4$—$SO_2$—NH—$C_1$-$C_4$ sulfonamide, or phenyl such that at least two of $R^2$, $R^3$, $R^4$, $R^5$, $R^6$, and $R^7$ are other than H.

The present invention is directed to another related substituted β-carboline compound having the structure where the X heteroatom is NH, N—$CH_3$, S, or O and $R^1$ is 1-naphthyl or 1-dihydroacenaphthenyl each optionally substituted with Br or F. The $R^2$-$R^7$ substituents are independently $R^2$, $R^3$, $R^4$, $R^5$, $R^6$, and $R^7$ are independently H, OH, Br, Cl, CN, $CH_3$, —$OCH_3$, —$OCF_3$, —$C(O)OCH_2CH_3$, —$CH_2$—$SO_2$—NH—$CH_3$, or phenyl with the proviso that when X is NH, $R^1$ is 1-naphthyl or 1-naphthyl substituted with Br or F and one of $R^5$, $R^6$, or $R^7$ is —$OCH_3$, then $R^2$, $R^3$, $R^4$, $R^5$, $R^6$, and $R^7$ are independently H, OH, Br, Cl, CN, —$OCF_3$, —C(O)$OCH_2CH_3$, —$CH_2$—$SO_2$—NH—$CH_3$, or phenyl such that at least two of $R^2$, $R^3$, $R^4$, $R^5$, $R^6$, and $R^7$ are other than H.

The present invention is directed further to a method for inhibiting proliferation of cells associated with a cell proliferative disease. The method comprises contacting the cells with an amount of one or more substituted β-carboline compounds or analogs thereof pharmacologically effective to inhibit proliferation of the cells. The present invention is directed to a related method where the proliferative disease-associated cells may comprise a cancerous tumor and the method further comprises contacting the tumor with one or more other anticancer drugs.

The present invention is directed further still to a synthetic β-carboline compound that is 1-furan-3-yl-6-methoxy-9H-β-carboline, 1-furan-3-yl-7-methoxy-9H-β-carboline, 1-pyridin-3-yl-7-methoxy-9H-β-carboline, 6-methoxy-1-quinolin-4-yl-9H-β-carboline, 7-methoxy-1-quinolin-4-yl-9H-β-carboline, 1-Isoquinolin-1-yl-7-methoxy-9H-β-carboline, 6-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 1-isoquinolin-4-yl-6-methoxy-9H-β-carboline, 1-isoquinolin-4-yl-7-methoxy-9H-β-carboline, 6-methoxy-1-quinolin-3-yl-9H-β-carboline, 7-methoxy-1-quinolin-3-yl-9H-β-carboline, 6-methoxy-1-naphthalen-1-yl-9H-β-carboline, 7-methoxy-1-naphthalen-1-yl-9H-β-carboline, 6-methoxy-1-quinolin-5-yl-9H-β-carboline, 7-methoxy-1-quinolin-5-yl-9H-β-carboline, 6-methoxy-1-quinolin-6-yl-9H-β-carboline, 1-isoquinolin-5-yl-6-methoxy-9H-β-carboline, 1-isoquinolin-5-yl-7-methoxy-9H-β-carboline, 6-methoxy-1-naphthalen-2-yl-9H-β-carboline, 7-methoxy-1-naphthalen-2-yl-9H-β-carboline, 1-anthracen-9-yl-6-methoxy-9H-β-carboline, 1-anthracen-9-yl-7-methoxy-9H-β-carboline, 6-methoxy-1-phenanthren-9-yl-9H-β-carboline, 7-methoxy-1-phenanthren-9-yl-9H-β-carboline, 6-methoxy-1-phenyl-9H-β-carboline, 7-methoxy-1-phenyl-9H-β-carboline, 6-methoxy-1-(2-methyl-naphthalen-1-yl)-9H-β-carboline, 7-methoxy-1-(2-methyl-naphthalen-1-yl)-9H-β-carboline, 6-methoxy-1-(6-methoxy-naphthalen-1-yl)-9H-β-carboline, 6-Benzyloxy-1-naphthalen-1-yl-9H-β-carboline, 8-methyl-1-naphthalen-1-yl-9H-β-carboline, 6-methoxy-1-(4-pyridin-2-yl-phenyl)-9H-β-carboline, 8-methoxy-1-(naphthalen-1-yl)-9H-pyrido[3,4-b]indole, 1-(naphthalen-1-yl)-9H-pyrido[3,4-b]indol-6-ol, 6-methoxy-1-(naphthalen-1-yl)-4-phenyl-9H-pyrido[3,4-b]indole, N-methyl-1-(1-(naphthalen-1-yl)-9H-pyrido[3,4-b]indol-6-yl)methane sulfonamide, 5-methyl-1-(naphthalen-1-yl)-9H-pyrido[3,4-b]indole, 1-(5-fluoronaphthalen-1-yl)-6-methoxy-9H-pyrido[3,4-b]indole, 1-(5-bromonaphthalen-1-yl)-6-methoxy-9H-pyrido[3,4-b]indole, 1-(5-bromonaphthalen-1-yl)-6-methyl-9H-pyrido[3,4-b]indole, 1-(1,2-dihydroacenaphthylen-5-yl)-6-methoxy-9H-pyrido[3,4-b]indole, 6-chloro-1-(naphthalen-1-yl)benzo[4,5]thieno[2,3-c]pyridine, 1-(naphthalen-1-yl)benzofuro[2,3-c]pyridine, 1-(naphthalen-1-yl)benzo[4,5]thieno[2,3-c]pyridine, 6-methyl-1-(naphthalen-1-yl)-9H-pyrido[3,4-b]indole, 1-(naphthalen-1-yl)-6-(trifluoromethoxy)-9H-pyrido[3,4-b]indole, 1-(naphthalen-1-yl)-9H-pyrido[3,4-b]indole-6-carbonitrile, 6-bromo-1-(naphthalen-1-yl)-9H-pyrido[3,4-b]indole, ethyl-6-methoxy-1-(naphthalen-1-yl)-9H-pyrido[3,4-b]indole-3-carboxylate, 9-methyl-1-(naphthalen-1-yl)-9H-pyrido[3,4-b]indole, or 6-methoxy-9-methyl-1-(naphthalen-1-yl)-9H-pyrido[3,4-b]indole. Mono- and multiple-azapyrido[b]indoles also anticipated, as well as g- and d-carbolines and their derivatives.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 5A-5F illustrate flow cytometry histograms comparing the effects of Compound 19 and Camptothecin treatment on the cell cycle kinetics of MCF-7 breast cancer cells.

FIGS. 6A-6F illustrate flow cytometry histograms comparing the effects of Compound 19 and Adriamycin treatment on the cell cycle kinetics of cultured normal human fibroblasts.

FIGS. 7A-7I illustrate flow cytometry histograms showing the effects of Compound 19 and Adriamycin or Camptothecin treatment on the cell cycle kinetics of A549 lung cancer cells.

FIGS. 8A-8I illustrate flow cytometry histograms showing the effects of Compound 19 and Adriamycin treatment on the cell cycle kinetics of HCT116 cells.

FIGS. 9A-9I illustrate flow cytometry histograms showing the effects of Compound 19 and Adriamycin treatment on the cell cycle kinetics of HCT116 cells.

FIGS. 10A-10I illustrate flow cytometry histograms showing the effects of Compound 19 and Adriamycin or Camptothecin treatment on the cell cycle kinetics of LNCaP cells.

FIGS. 11A-11I illustrate flow cytometry histograms showing the effects of Compound 19 and Adriamycin or Camptothecin treatment on the cell cycle kinetics of DU145 cells.

FIGS. 12A-12I illustrate flow cytometry histograms showing the effects of Compound 19 and Adriamycin or Camptothecin treatment on the cell cycle kinetics of PC-3 lung cancer cells.

DETAILED DESCRIPTION OF THE INVENTION

Figure 1:
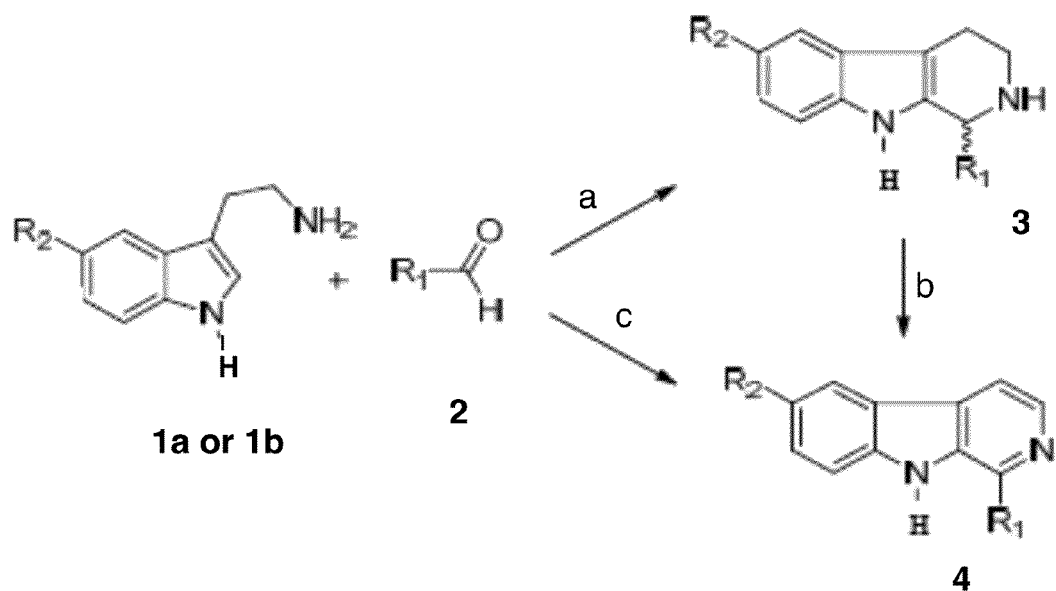
FIG. 1 is a synthetic scheme for the general synthesis of substituted β-carboline compounds.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device, compound, composition, or method described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the terms "compound", "1-aryl(heteroaryl) pyrido[b]indole compound" or "substituted β-carboline compound" may be interchangeable and refer to a chemically synthesized molecular entity or derivatives or analogs thereof, including salts or hydrates, that blocks, stops, inhibits, and/or suppresses cancer cell proliferation and treats the cancer or tumor associated therewith. As would be apparent to one of ordinary skill in the art "aryl" and "heteroaryl" refer to any functional group or substituent derived from a simple aromatic ring(s) or a simple aromatic ring(s) containing a heteroatom, preferably in this instance nitrogen, oxygen or sulfur.

As used herein, the term "contacting" refers to any suitable method of bringing one or more of the compounds described herein with or without one or more other therapeutic agents into contact with one or more cancer cells or a tumor comprising the same. In vitro or ex vivo this is achieved by exposing the cancer cells or tumor to the compound(s)/therapeutic agent(s) in a suitable medium. For in vivo applications, any known method of administration is suitable as described herein.

As used herein, the terms "effective amount", "pharmacologically effective amount" or "therapeutically effective amount" are interchangeable and refer to an amount that results in an antiproliferative effect against cancer cells in vitro or an improvement or remediation in the cancer in vivo. Those of skill in the art understand that the effective amount may improve the patient's or subject's condition, but may not be a complete cure of the cancer.

As used herein, the term "treating" or the phrase "treating a cancer" includes, but is not limited to, halting the growth of the cancer, killing the cancer, or reducing the size of the cancer. Halting the growth refers to halting any increase in the size or the number of or size of the cancer cells or to halting the division of the cancer cells. Reducing the size refers to reducing the size of the tumor associated with the cancer or the number of or size of the cancer cells.

As used herein, the term "subject" refers to any target of the treatment.

In one embodiment of the present invention, there is provided β-carbolines having the structure:

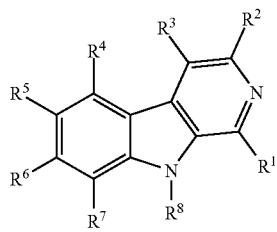

where $R^1$ is phenyl, naphthyl, anthracyl, phenanthracyl, quinolinyl, isoquinolinyl, quinoxalinyl, or phenyl substituted with pyridinyl, or $C_1$-$C_4$ alkyl or $C_1$-$C_4$ alkoxy derivatives thereof; and $R^2$-$R^8$ are independently hydrogen, $C_1C_4$ alkyl, $C_1$-$C_4$ alkoxy, $C_1$-$C_4$ alkoxyphenyl, halogen, thiol, alkylthiol, sulfonyl, sulfonamide, amide, substituted amide, ester, nitrile, OH, amino, substituted amine, haloalkyl, haloalkoxy, or acyl. Particularly, for example, $R^1$ may be 2-, 3-, 4-, 5-, 6-, or 7-benzofuranyl, 2-, 3-, 4-, 5-, 6-, or 7-indolyl, 2-, 3-, 4-, 5-, 6-, or 7-benzothiophenyl, 1-, 2-, 3-, 4-, 5-, or 6-indenyl, 2-, 4-, 5-, 6- or 7-benzoxazolyl, 2-, 4-, 5-, 6- or 7-benzimidazolyl, 2-, 4-, 5-, 6- or 7-benzothiazolyl, 3-furanyl, 3-pyridinyl, 3-, 4- or 5-quinolinyl, 1-, 4- or 5-isoquinolinyl, 5- or 6-quinoxalinyl, 1-naphthyl, 2-methyl- or 6-methoxy-naphthalen-1-yl, 9-anthracyl, 9-phenanthracyl, 1-phenyl, 4-pyridin-2-yl-phenyl, or a group having the structure:

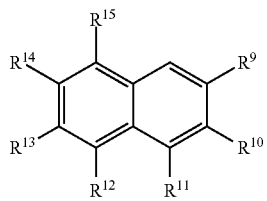

where $R^9$-$R^{15}$ may independently be $C_1$-$_4$ alkyl, $C_{14}$ alkoxy, halogen, $C_{14}$ alkylthiol, sulfonyl, sulfonamide, amide, substituted amide, ester, nitrile, hydroxyl, amino, substituted amine, $C_{14}$ haloalkyl, $C_{14}$ haloalkoxy, acyl, aryl, heteroaryl or derivative thereof; and where $R^2$-$R^4$ may be H; $R^5$ may be —OCH$_3$, —OCH$_2$(phenyl) or H; $R^6$ may be —OCH$_3$ or H; $R^7$ may be —CH$_3$ or H; and $R^8$ may be H.

In one aspect of this embodiment $R^1$ may be 3-furanyl, 3-, 4- or 5-quinolinyl, 4- or 5-isoquinolinyl, 5- or 6-quinoxalinyl, 1- or 2-naphthyl, 2-methyl- or 6-methoxy-napththalen-1-yl, 9-anthracyl, 9-phenanthracyl, 1-phenyl, or 4-pyridin-2-yl-phenyl; $R^5$ may be —OCH$_3$; and $R^6$-$R^7$ may be H.

In another aspect of this embodiment $R^1$ may be 3-furanyl, 3-pyridinyl, 3-, 4- or 5-quinolinyl, 1-, 4- or 5-isoquinolinyl, 5- or 6-quinoxalinyl, 1- or 2-naphthyl, 2-methyl-napththalen-1-yl, 9-anthracyl, 9-phenanthracyl, or 1-phenyl; $R^6$ may be —OCH$_3$; and $R^5$ and $R^7$ may be H.

In yet another aspect of this embodiment $R^1$ may be 1-naphthyl; $R^2$ may be H; $R^6$—OCH$_2$(phenyl); and $R^5$ and $R^7$ may be H.

In yet another aspect of this embodiment $R^1$ may be 1-naphthyl; $R^5$ and $R^6$ may be H; and $R^7$ may be —CH$_3$.

In one embodiment of the present invention, there is provided a substituted β-carboline having the structure:

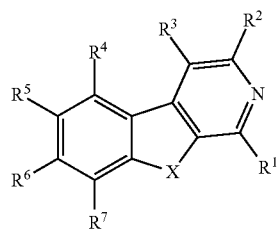

where X is NH, N—$C_1$-$C_4$ alkyl, S, or O; $R^1$ is furanyl, 1-naphthyl, 1-dihydroacenaphthenyl, anthracyl, phenanthracyl, 3-quinolinyl, 5-quinolinyl, isoquinolinyl, quinoxalinyl, phenyl substituted with pyridinyl each optionally substituted with a halogen, $C_1$-$C_4$ alkyl, or $C_1$-$C_4$ alkoxy; and $R^2$, $R^3$, $R^4$, $R^5$, $R^6$, and $R^7$ are independently H, OH, halogen, CN, $C_1$-$C_4$ alkyl, $C_1$-$C_4$ alkoxy, $C_1$-$C_4$ haloalkyl, $C_1$-$C_4$ haloalkoxy, —C(O)O$C_1$-$C_4$ ester, —$C_1$-$C_4$—$SO_2$—NH—$C_1$-$C_4$ sulfonamide, phenyl, $C_1$-$C_4$ alkoxyphenyl; where when X is NH, at least one of $R^2$, $R^3$, $R^4$, $R^5$, $R^6$, and $R^7$ is other than H.

In one aspect of this embodiment X may be NH; $R^1$ may be furanyl, 1-naphthyl, anthracyl, phenanthracyl, 3-quinolinyl, 5-quinolinyl, isoquinolinyl, quinoxalinyl, phenyl substituted with pyridinyl each optionally substituted with $C_1$-$C_4$ alkyl, or $C_1$-$C_4$ alkoxy; and $R^2$, $R^3$, $R^4$, $R^5$, $R^6$, and $R^7$ independently may be —H, $C_1$-$C_4$ alkyl, $C_1$-$C_4$ alkoxy, $C_1$-$C_4$ alkoxyphenyl; wherein one of $R^5$, $R^6$ or $R^7$ is $C_1$-$C_4$ alkoxy or $C_1$-$C_4$ alkoxyphenyl.

In another aspect of this embodiment X may be NH; $R^1$ may be 3-furanyl, 3-quinolinyl, 5-quinolinyl, 1-isoquinolinyl, 4-isoquinolinyl, 5-isoquinolinyl, 5-quinoxalinyl, 6-quinoxalinyl, 1-naphthyl, 2-methyl-1-naphthyl, 6-methoxy-1-naphthyl, 9-anthracyl, 9-phenanthracyl, 4-pyridin-2-yl-phenyl, or a group with the structure:

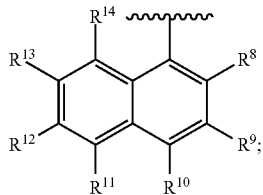

$R^8$, $R^9$, $R^{19}$, $R^{11}$, $R^{12}$, $R^{13}$, and $R^{14}$ independently may be $C_1$-$C_4$ alkyl or $C_1$-$C_4$ alkoxy; $R^2$, $R^3$, and $R^4$ may be H; $R^5$ may be —OCH$_3$, —OCH$_2$(phenyl), or H; $R^6$ may be —OCH$_3$ or H; and $R^7$ may be —CH$_3$ or H; where (1) $R^5$ is —OCH$_3$ or —OCH$_2$(phenyl) when $R^6$ is H, or (2) $R^5$ is H when $R^6$ is —OCH$_3$.

In yet another aspect of this embodiment X may be NH; $R^1$ may be 1-naphthyl or 1-dihydroacenaphthenyl where each optionally may be substituted with Br or F; $R^2$, $R^3$, $R^4$, $R^5$, $R^6$, and $R^7$ independently may be H, OH, halogen, CN, $C_1$-$C_4$ alkyl, $C_1$-$C_4$ alkoxy, phenyl, $C_{1-r}$ $C_4$ haloalkyl, $C_1$-$C_4$ haloalkoxy, —C(O)O$C_1$-$C_4$ ester, —($C_1$-$C_4$)—$SO_2$—NH—($C_1$-$C_4$) sulfonamide, or phenyl; wherein at least one of $R^2$, $R^3$, $R^4$, $R^5$, $R^6$, and $R^7$ is other than —H. In yet another aspect of this embodiment X may be N—CH$_3$, S, or O; $R^1$ may be 1-naphthyl or 1-dihydroacenaphthenyl each optionally substituted with Br or F; $R^2$, $R^3$, $R^4$, $R^5$, $R^6$, and $R^7$ independently may be H, OH, halogen, CN, $C_1$-$C_4$ alkyl, $C_1$-$C_4$ alkoxy, phenyl, $C_1$-$C_4$ haloalkyl, $C_1$-$C_4$ haloalkoxy, —C(O)O$C_1$-$C_4$ ester, —$C_1$-$C_4$—$SO_2$—NH—$C_1$-$C_4$ sulfonamide or phenyl.

In a related embodiment of the present invention invention, there is provided a substituted β-carboline compound having the structure:

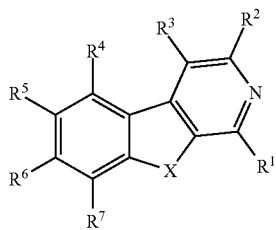

where X is NH, N—$C_1$-$C_4$ alkyl, S, or O; $R^1$ is 1-naphthyl or 1-dihydroacenaphthenyl, each optionally substituted with a halogen; and $R^2$, $R^3$, $R^4$, $R^5$, $R^6$, and $R^7$ are independently H, OH, halogen, CN, $C_1$-$C_4$ alkyl, $C_1$-$C_4$ alkoxy, $C_1$-$C_4$ haloalkoxy, —C(O)O$C_1$-$C_4$ ester, —$C_1$-$C_4$—$SO_2$—NH—$C_1$-$C_4$ sulfonamide, or phenyl; where, when X is NH, $R^1$ is 1-naphthyl or 1-naphthyl substituted with a halogen and one of $R^5$, $R^6$, or $R^7$ is $C_1$-$C_4$ alkoxy, then $R^2$, $R^3$, $R^4$, $R^5$, $R^6$, and $R^7$ are independently H, OH, halogen, CN, $C_1$-$C_4$ haloalkoxy, —C(O)O$C_1$-$C_4$ ester, —$C_1$-$C_4$—$SO_2$—NH—$C_1$-$C_4$ sulfonamide, or phenyl such that at least two of $R^2$, $R^3$, $R^4$, $R^5$, $R^6$, and $R^7$ are other than H.

In one aspect of this related embodiment X may be NH; $R^1$ may be 1-naphthyl optionally substituted with Br or F; and $R^2$, $R^3$, $R^4$, $R^5$, $R^6$, and $R^7$ may be independently H, OH, halogen, CN, $C_1$-$C_4$ alkyl, $C_1$-$C_4$ alkoxy, $C_1$-$C_4$ haloalkoxy, —C(O)O$C_1$-$C_4$ ester, —($C_1$-$C_4$)—$SO_2$—NH—($C_1$-$C_4$) sulfonamide, or phenyl; where, when one of $R^5$, $R^6$, or $R^7$ is $C_1$-$C_4$ alkoxy, then $R^2$, $R^3$, $R^4$, $R^5$, $R^6$, and $R^7$ are independently H, OH, halogen, CN, $C_1$-$C_4$ haloalkoxy, —C(O)O$C_1$-$C_4$ ester, —$C_1$-$C_4$—$SO_2$—NH—$C_1$-$C_4$ sulfonamide, or phenyl such that at least two of $R^2$, $R^3$, $R^4$, $R^5$, $R^6$, and $R^7$ are other than H.

In another aspect X may be NH; $R^1$ may be 1-dihydroacenaphthenyl optionally substituted with Br or F; and $R^2$, $R^3$, $R^4$, $R^5$, $R^6$, and $R^7$ may be independently H, OH, halogen, CN, $C_1$-$C_4$ alkyl, $C_1$-$C_4$ alkoxy, phenyl, $C_1$-$C_4$ haloalkoxy, —C(O)O$C_1$-$C_4$ ester, —($C_1$-$C_4$)—$SO_2$—NH—($C_1$-$C_4$) sulfonamide, or phenyl.

In yet another aspect X may be N—CH$_3$, S, or O; $R^1$ may be 1-naphthyl or 1-dihydroacenaphthenyl each optionally substituted with Br or F; and $R^2$, $R^3$, $R^4$, $R^5$, $R^6$, and $R^7$ may be independently H, OH, halogen, CN, $C_1$-$C_4$ alkyl, $C_1$-$C_4$ alkoxy, phenyl, $C_1$-$C_4$ haloalkoxy, —C(O)O$C_1$-$C_4$ ester, —$C_1$-$C_4$—$SO_2$—NH—$C_1$-$C_4$ sulfonamide or phenyl.

In another related embodiment of the present invention, there is provided a substituted β-carboline compound having the structure:

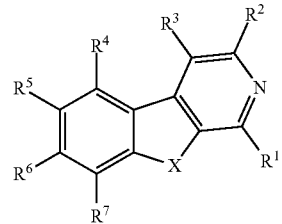

where X is NH, N—CH$_3$, S, or O; $R^1$ is 1-naphthyl or 1-dihydroacenaphthenyl each optionally substituted with Br or F; and $R^2$, $R^3$, $R^4$, $R^5$, $R^6$, and $R^7$ are independently H, OH, Br, Cl, CN, CH$_3$, —OCH$_3$, —OCF$_3$, —C(O)OCH$_2$CH$_3$, —CH$_2$—$SO_2$—NH—CH$_3$, or phenyl; wherein, when X is NH, $R^1$ is 1-naphthyl or 1-naphthyl substituted with Br or F and one of $R^5$, $R^6$, or $R^7$ is —OCH$_3$, then $R^2$, $R^3$, $R^4$, $R^5$, $R^6$, and $R^7$ are independently H, OH, Br, Cl, CN, —OCF$_3$, —C(O)OCH$_2$CH$_3$, —CH$_2$—$SO_2$—NH—CH$_3$, or phenyl such that at least two of $R^2$, $R^3$, $R^4$, $R^5$, $R^6$, and $R^7$ are other than H.

In one aspect of this embodiment X may be NH; $R^1$ may be 1-naphthyl; $R^2$ may be H or C(O)OCH$_2$CH$_3$; $R^3$ may be H or phenyl; $R^4$ may be H or CH$_3$; $R^5$ may be H, OH, Cl, Br, CN, CH$_3$, —OCH$_3$, —OCF, or —CH$_2$SO$_2$NHCH$_3$; $R^6$ may be H; and $R^7$ may be H or OCH$_3$.

In another aspect of this embodiment X may be NH; $R^1$ may be 1-(5-flour-naphthyl) or 1-(5-bromo-naphthyl); $R^2$, $R^3$, $R^4$, $R^6$, and $R^7$ may be H; and $R^5$ may be $OCH_3$ or $CH_3$.

In yet another aspect of this embodiment wherein X may be NH; $R^1$ may be 1-dihydroacenaphthenyl; $R^2$, $R^3$, $R^4$, $R^6$, and $R^7$ may be H; and $R^5$ may be $OCH_3$.

In yet another aspect of this embodiment X may be $N—CH_3$; $R^1$ may be 1-naphthyl; $R^2$, $R^3$, $R^4$, $R^6$, and $R^7$ may be H; and $R^5$ may be H or $OCH_3$.

In yet another aspect of this embodiment X may be S or O; $R^1$ may be 1-naphthyl; $R^2$, $R^3$, $R^4$, $R^6$, and $R^7$ may be H; and $R^5$ may be H or Cl.

In yet another embodiment of the present invention, there is provided a synthetic β-carboline compound or analog thereof that is 1-furan-3-yl-6-methoxy-9H-β-carboline, 1-furan-3-yl-7-methoxy-9H-β-carboline, 1-pyridin-3-yl-7-methoxy-9H-β-carboline, 6-methoxy-1-quinolin-4-yl-9H-β-carboline, 7-methoxy-1-quinolin-4-yl-9H-β-carboline, 1-Isoquinolin-1-yl-7-methoxy-9H-β-carboline, 6-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 1-isoquinolin-4-yl-6-methoxy-9H-β-carboline, 1-isoquinolin-4-yl-7-methoxy-9H-β-carboline, 6-methoxy-1-quinolin-3-yl-9H-β-carboline, 7-methoxy-1-quinolin-3-yl-9H-β-carboline, 6-methoxy-1-naphthalen-1-yl-9H-β-carboline, 7-methoxy-1-naphthalen-1-yl-9H-β-carboline, 6-methoxy-1-quinolin-5-yl-9H-β-carboline, 7-methoxy-1-quinolin-5-yl-9H-β-carboline, 6-methoxy-1-quinolin-5-yl-9H-β-carboline, 1-isoquinolin-5-yl-6-methoxy-9H-β-carboline, 1-isoquinolin-5-yl-7-methoxy-9H-β-carboline, 6-methoxy-1-naphthalen-2-yl-9H-β-carboline, 7-methoxy-1-naphthalen-2-yl-9H-β-carboline, 1-anthracen-9-yl-6-methoxy-9H-β-carboline, 1-anthracen-9-yl-7-methoxy-9H-β-carboline, 6-methoxy-1-phenanthren-9-yl-9H-β-carboline, 7-methoxy-1-phenanthren-9-yl-9H-β-carboline, 6-methoxy-1-phenyl-9H-β-carboline, 7-methoxy-1-phenyl-9H-β-carboline, 6-methoxy-1-(2-methyl-naphthalen-1-yl)-9H-β-carboline, 7-methoxy-1-(2-methyl-naphthalen-1-yl)-9H-β-carboline, 6-methoxy-1-(6-methoxy-naphthalen-1-yl)-9H-β-carboline, 6-Benzyloxy-1-naphthalen-1-yl-9H-β-carboline, 8-methyl-1-naphthalen-1-yl-9H-β-carboline, 6-methoxy-1-(4-pyridin-2-yl-phenyl)-9H-β-carboline, 8-methoxy-1-(naphthalen-1-yl)-9H-pyrido[3,4-b]indole, 1-(naphthalen-1-yl)-9H-pyrido[3,4-b]indol-6-ol, 6-methoxy-1-(naphthalen-1-yl)-4-phenyl-9H-pyrido[3,4-b]indole, N-methyl-1-(1-(naphthalen-1-yl)-9H-pyrido[3,4-b]indol-6-yl)methane sulfonamide, 5-methyl-1-(naphthalen-1-yl)-9H-pyrido[3,4-b]indole, 1-(5-fluoronaphthalen-1-yl)-6-methoxy-9H-pyrido[3,4-b]indole, 1-(5-bromonaphthalen-1-yl)-6-methoxy-9H-pyrido[3,4-b]indole, 1-(5-bromonaphthalen-1-yl)-6-methyl-9H-pyrido[3,4-b]indole, 1-(1,2-dihydroacenaphthylen-5-yl)-6-methoxy-9H-pyrido[3,4-b]indole, 6-chloro-1-(naphthalen-1-yl)benzo[4,5]thieno[2,3-c]pyridine, 1-(naphthalen-1-yl)benzofuro[2,3-c]pyridine, 1-(naphthalen-1-yl)benzo[4,5]thieno[2,3-c]pyridine, 6-methyl-1-(naphthalen-1-yl)-9H-pyrido[3,4-b]indole, 1-(naphthalen-1-yl)-6-(trifluoromethoxy)-9H-pyrido[3,4-b]indole, 1-(naphthalen-1-yl)-9H-pyrido[3,4-b]indole-6-carbonitrile, 6-bromo-1-(naphthalen-1-yl)-9H-pyrido[3,4-b]indole, ethyl-6-methoxy-1-(naphthalen-1-yl)-9H-pyrido[3,4-b]indole-3-carboxylate, 9-methyl-1-(naphthalen-1-yl)-9H-pyrido[3,4-b]indole, or 6-methoxy-9-methyl-1-(naphthalen-1-yl)-9H-pyrido[3,4-b]indole.

In these embodiments the substituted β-carboline compound or analog may be a pharmacologically effective salt or hydrate thereof. Also, the substituted β-carboline or analog may be a pharmaceutical composition further comprising a pharmaceutically effective carrier.

In yet another embodiment of the present invention, there is provided a method for inhibiting proliferation of cells associated with a cell proliferative disease, comprising contacting the cells with an amount of one or more substituted β-carboline compounds or analogs thereof, as described supra, pharmacologically effective to inhibit proliferation of the cells. Further to this embodiment, the proliferative disease-associated cells may comprise a cancerous tumor, where the method comprises contacting the tumor with one or more other anticancer drugs. In this further embodiment the cancerous tumor may be contacted with the one or more anticancer drugs concurrently with or sequentially to contact with the one or more substituted β-carboline compounds or analogs. In both embodiments the cells may be breast cancer cells, colon cancer cells, prostate cancer cells, lung cancer cells, or pancreatic cancer cells and the cancerous tumor may be a breast cancer, a colon cancer, a prostate cancer, a pancreatic cancer, or a lung cancer.

Provided herein are chemically synthesized 1-aryl- or 1-heteroarylpyrido[b]indole compounds (1-aryl(heteroaryl)pyrido[b]indole), including derivatives and analogs thereof. These compounds exhibit antiproliferative effects against cell proliferative diseases, such as cancers. Without being limiting, for example, the compounds provided herein are effective against breast cancers, colon cancers, prostate cancers, or pancreatic cancers. Chemical syntheses of these 1-aryl(heteroaryl)pyrido[b]indole compounds are provided in Example 1.

Generally, the 1-aryl(heteroaryl)pyrido[b]indole compounds are small molecule aromatic structures having the chemical structure:

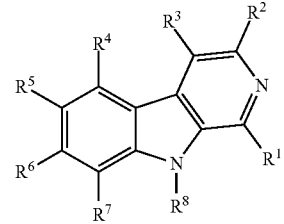

These compounds comprise a β-carboline having an aryl or heteroaryl substituent at C1 on the pyridine moiety. In addition, the indole moiety comprising the β-carboline may be substituted at one or more of C3-C8 and N9 in the pyrido[b]indole ring.

For example, without being limiting, $R^1$ aryl or heteroaryl substituent's at C1 may be phenyl, furanyl, pyridinyl, naphthyl, anthracyl, phenanthracyl, quinolinyl, isoquinolinyl, quinoxalinyl, or phenyl substituted with pyridinyl. It is contemplated that these aryl and heteroaryl substituent's may be substituted with short chain $C_{14}$ alkyl or alkoxy groups, particularly methyl or methoxy. For example, and without limiting possible substituents, $R^1$ may be a 2-, 3-, 4-, 5-, 6-, or 7-benzofuranyl, 2-, 3-, 4-, 5-,6-, or 7-indolyl, 2-, 3-, 4-, 5-, 6-, or 7-benzothiophenyl, 1-, 2-, 3-, 4-, 5-, or 6-indenyl, 2-, 4-, 5-, 6- or 7-benzoxazolyl, 2-, 4-, 5-, 6- or 7-benzimidazolyl, 2-, 4-, 5-, 6- or 7-benzothiazolyl 3-furanyl, 3-pyridinyl, 3-, 4- or 5-quinolinyl, 1-, 4- or 5-isoquinolinyl, 5-quinoxalinyl, 1- or 2-naphthalenyl, 2-methyl- or 6-methoxy -napththalen-1-yl, 9-anthracenyl, 9-phenanthrenyl, phenyl, or 4-pyridin -2-yl-phenyl. Alternatively, $R^1$ may be a group having the structure;

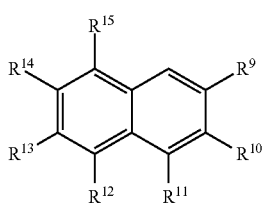

where the $R^9$, $R^{10}$, $R^{11}$, $R^{12}$, $R^{13}$, $R^{14}$ and $R^{15}$ may independently be $C_1$-$C_4$ alkyl, $C_1$-$C_4$ alkoxy, halogen, $C_1$-$C_4$ alkylthiol, sulfonyl, sulfonamide, amide, substituted amide, ester, nitrile, hydroxyl, amino, substituted amine, $C_1$-$C_4$ haloalkyl, $C_1$-$C_4$ haloalkoxy, acyl, aryl, heteroaryl or derivative thereof.

Generally, $R^2$, $R^3$, $R^4$, $R^5$, $R^6$, $R^7$ and $R^8$ substituents at C3-C8 and N9 may be hydrogen or short chain $C_1$-$C_4$ alkyl, alkoxy or aryloxy groups, particularly methyl, methoxy or benzyloxy; halogen, thiol, alkylthio, sulfonyl, sulfomainde, amide, substituted amide, ester, nitrile, hydroxy, amino, substituted amine, haloalkyl, haloalkoxy or acyl. Examples of 1-aryl(heteroaryl)pyrido[b]indole compounds, particularly β-carboline derivatives are provided in Example 2.

An alternative structure encompassing 1-aryl(heteroaryl)pyrido[b]indole compounds includes heteroatom analogs of the indole ring, particularly a substituted nitrogen, sulfur and oxygen. These compounds have the general chemical structure of

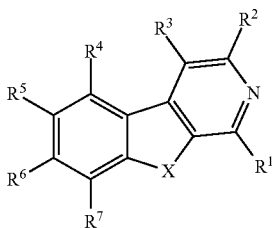

where the heteroatom X is nitrogen, sulfur, or oxygen or a substituted nitrogen, such as, but not limited to, a $C_1$-$C_4$ alkyl, preferably a methyl. $R^1$ may be any substituent as described supra, but preferably $R^1$ is 1-napthyl or 1-dihydroacenaphthenyl. Optionally, the $R^1$ substituent's may be substituted with a halogen, such as, bromine or fluorine. Particularly, the $R^2$-$R^7$ substituents independently may be hydrogen, hydroxy, methyl, methoxy, chlorine, bromine, cyano, trifluoromethoxy, phenyl, a $C_1$-$C_4$ dialkyl ester, for example, methylethyl ester, and a $C_1$-$C_4$ alkyl sulfonamide, for example, N-methyl methanesulfonamide.

Thus, the 1-aryl(heteroaryl)pyrido[b]indole compounds and analogs provided herein are useful as therapeutics. The compounds provided herein may be used to treat any subject, preferably a human, having a cell proliferative disease, such as a cancer, for example, but not limited to, a breast cancer, a colon cancer, a prostate cancer or a pancreatic cancer. It is contemplated that contacting the cancer cells comprising a cancer or tumor with one or more of these 1-aryl(heteroaryl)pyrido[b]indole compounds, particularly substituted beta-carbolines is effective to at least inhibit, reduce or prevent cancer cell proliferation or tumor growth. The compounds of the present invention may be administered alone or in combination or in concurrent therapy with other chemotherapeutic agents or pharmaceuticals which affect cancer pathology.

The present invention also provides therapeutic methods employing compositions comprising the 1-aryl(heteroaryl) pyrido[b]indole compounds disclosed herein. Preferably, these compositions include pharmaceutical compositions comprising a therapeutically or pharmacologically effective amount of one or more of the 1-aryl(heteroaryl)pyrido[b] indole compounds along with a pharmaceutically acceptable carrier. Also, these compositions include pharmacologically effective salts or hydrates thereof.

As is well known in the art, a specific dose level of chemotherapeutic compounds, such as the 1-aryl(heteroaryl)pyrido [b]indole compounds or related derivative or analog compounds thereof for any particular patient depends upon a variety of factors including the activity of the specific compound employed, the age, body weight, general health, sex, diet, time of administration, route of administration, rate of excretion, drug combination, and the progression or remission of the cancer. The person responsible for administration is well able to determine the appropriate dose for the individual subject and whether a suitable dosage of either or both of the substituted β-carbinols compound(s) and other chemotherapeutic agent(s) or drug(s) comprises a single administered dose or multiple administered doses.

The following example(s) are given for the purpose of illustrating various embodiments of the invention and are not meant to limit the present invention in any fashion.

EXAMPLE 1

Chemical Synthesis of β-carbolines
Methods and Materials

All the chemicals and solvents were purchased from Aldrich and used without further purification. All the reactions were performed under nitrogen atmosphere. TLC monitored progress of all the reaction on silica gel plates (Analtech, Inc.). Fisher scientific Da visil grade 1740 (170-400 mesh) was used for flash chromatography to purify the final products. $^1$H NMR spectra were recorded on Brucker AR, 300-MHz spectrometer: chemical shifts are expressed in δ values (ppm) reference to the TMS and coupling constants (J values) in Hz. Mass spectral data were determined on a Brucker-HP Esquire-LC spectrometer (ESI-MS). Elemental analysis (C, H, N) was performed by Atlantic Microlab, Inc. (Norcross, G A) and results were within ±0.4% of the theoretical values for the formula given.

The purity of all other beta-carbolines was determined by HPLC from our laboratory. The analysis was carried out using a SUPELCOSIL® 5 μm C-18 reverse phase column (250×4.6 mm) at ambient temperature on a Waters® 2695 HPLC system equipped with the 996 photodiode array detector. Isocratic method comprising 5% water (solvent A) and 95% methanol (solvent B) was used. 10 min run time was set at a flow-rate of 1.75 mL/min. Area % purity was detected at 230 nm or 300 nm. The purity of all compounds was found to be in the range 95 to 99.9%.

General Procedure for the Synthesis of Tetrahydro β-carbolines

As shown in FIG. 1, a C5-substituted tryptamine 1a or C6-substituted tryptamine 1b, (0.524 mmol) and appropriate aryl or heteroaryl aldehyde 2 (0.63 mmol) were dissolved in THF (20 mL). The reaction mixture was cooled to 0° C. $CF_3COOH$ (0.2 ml) was then added at 0° C., and the reaction mixture was then allowed to stir at 0° C. for 1 hr. The ice bath was then removed and the reaction allowed to stir for a further 1 hr from 0° C. to r.t. The reaction mixture was quenched with aqueous saturated $NaHCO_3$ (5 ml) and the organic phase separated. The mixture was extracted with EtOAc (2×10 ml). The combined organic phase was dried over anhydrous $NaSO_4$ and filtered and organic solvents were evaporated under reduced pressure to give the crude product tetrahydro β-carboline 3. The crude product was directly used for second step without further purification.

General Procedure for the Synthesis of β-carbolines

To a solution of the crude tetrahydro β-carboline 3 in xylene (10 ml) was added 10% Pd/C (50-100 mg) and the mixture refluxed overnight. The reaction mixture was then cooled and filtered through celite and washed with MeOH (5-10 ml). Evaporation of the xylene/MeOH filtrate under reduced pressure yielded a crude β-carboline residue. The crude residue was subjected to flash chromatography (30% ethyl acetate in hexanes) to obtain pure β-carbolines 4 in 50-75% overall yield.

General Procedure for the Synthesis of 7-Hydroxy β-carbolines

βcarboline derivative (0.02 mmol) in dry methylene chloride was cooled to −60° C. and boron tribromide (0.06 mmol) of 1M solution in methylene chloride was added drop-wise over a period of 5-10 minutes to the reaction flask at the same temperature. After stirring the reaction mixture for 2 days at room temperature, it was quenched with methanol (10 mL) at −30° C. and again the mixture was allowed to stir for 4 hours. Methanol was evaporated under reduced pressure and the residue was repeatedly evaporated with methanol and was recrystallized with methanol.

Single Step General Microwave Synthesis of β-carbolines

Tryptamines (0.62 mmol) and aldehydes (0.75 mmol) were dissolved in 4 mL methylene chloride in round bottomed flask. If tryptamines (hydrochloride salts) were insoluble in methylene chloride in those cases few drops of methanol was added to the mixture dissolve tryptamines completely to make homogeneous solution mixture. Catalyst was prepared separately by mixing 21 mg of 10% Pd/C and 500 mg of montmorillonite K-10. This catalyst was added to the above reaction mixture and stirred for nearly 5-10 minutes and solvents were removed under reduced pressure. The dried solid mixture was transferred to 10 mL microwave reaction vial (CEM vials) and irradiated in the CEM Discover labmate microwave reactor for 60 minutes at 150° C. using 100 psi pressure and 100 watt power. After the completion of reaction, methylene chloride was added or in some case (where tryptamine hydrochloride was used) mixture of methanol and ethyl acetate were added and filtered through the filtering agent celite. The filtrate was concentrated under reduced pressure and crude residue was subjected to the column chromatography using ethyl acetate and hexane solvent mixture (3:7) to obtain β-carbolines in 22-60% yields.

EXAMPLE 2

Synthetic β-carboline Derivatives and Analogs

1-Pyridin-3-yl-7-methoxy-9H-β-carboline 5

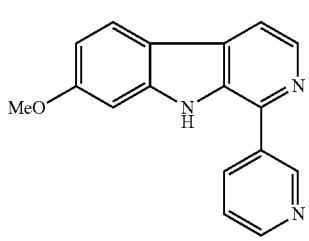 [SMILES: COc1ccc2c(c1)[nH]c1c(-c3cccnc3)nccc12]

$^1$H NMR $(CD_3)_2CO$-d 3.92 (s, 3H), 6.93 (1H, dd, J=2.25 Hz and 8.72 Hz), 7.09 (1H, d, J=2.18 Hz), 7.69 (1H, dd J=4.96 Hz and 7.91 Hz), 8.03 (d, 1H, J=5.34 Hz), 8.08 (d, 1H, J=8.72 Hz), 8.36 (t, 1H), 8.39 (d, 1H, J=5.34 Hz), 8.71 (dd, 1H, J=1.71 Hz and 4.96 Hz), 9.09 (d, 1H, J=1.71 Hz). Anal. calculated for C17H13N3O. 0.1H$_2$O, (CHN): C, 73.68; H, 4.80; N, 15.16. found C, 73.32; H, 4.76; N, 14.88, MS: m/z 276.2 (MH$^+$), m.pt: 216-217° C. MS: m/z 276.3 (MH$^+$). (yield 81%).

1-Furan-3-yl-9H-β-carbolin-7-ol 6

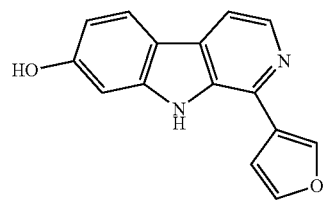 [SMILES: Oc1ccc2c(c1)[nH]c1c(-c3ccoc3)nccc12]

$^1$H NMR (DMSO-d6): δ 12.12 (bs, 1H, OH), 10.55 (bs, 1H, NH), 8.82 (s, 1H, ArH), 8.62-8.30 (m, 3H, ArH), 8.14 (d, J=7.8 Hz, 1H, ArH), 7.36 (s, 1H, ArH), 7.24-7.03 (m, 1H, ArH), 6.93 (d, J=8.1 Hz, 1H, ArH); MS (ESI); m/z 251 [M+H]$^+$; Anal. Calcd. $(C_{15}H_{10}N_2O_2)$ C, H, N.

1-Isopropyl-9H-β-carbolin-7-ol 7

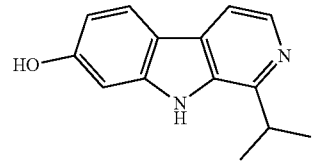 [SMILES: CC(C)c1nccc2c1[nH]c1cc(O)ccc12]

$^1$H NMR (DMSO-d6): δ 12.48 (bs, 1H, OH), 10.50 (bs, 1H, NH), 8.46-8.25 (m, 3H, ArH), 7.05 (s, 1H, ArH), 6.90 (d, J=9 Hz, 1H, ArH), 3.95-3.81 (m, 1H, CH), 1.52 (s, 3H, CH$_3$) & 1.50 (s, 3H, CH$_3$); MS (ESI); m/z 227 [M+H]$^+$; Anal. Calcd. $(C_{14}H_{14}N_2O)$C, H, N.

1-Furan-3-yl-7-methoxy-9H-β-carboline 8

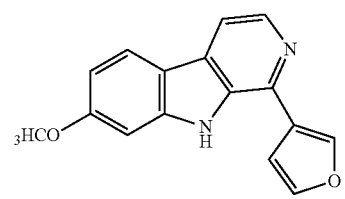

$^1$H NMR [300 MHz, $(CD_3)_2CO$]: d 3.92 (s, 3H), 6.92 (1H, dd, J=2.25 Hz and 8.67 Hz), 7.16 (1H, d, J=2.25 Hz), 7.27 (dd, 1H, J=0.79 Hz and 1.82 Hz), 7.77 (t, 1H), 7.91 (d, 1H, J=5.18 Hz), 8.11 (d, 1H, J=8.67 Hz), 8.39 (d, J=5.18 Hz, 1H), 8.46 (d, J=0.79 Hz, 1H), 10.37 (bs, 1H). MS: m/z 265.1 (MH⁺), 401.5 (m+Na). m.pt: 203-204° C. (yield 56%).

1-Furan-3-yl-6-methoxy-9H-β-carboline 9

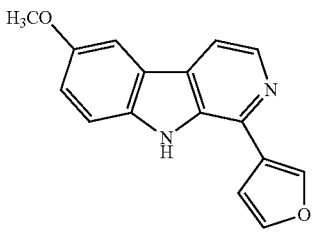 [SMILES: COc1ccc2[nH]c3c(-c4ccoc4)nccc3c2c1]

¹H NMR (CDCl₃): δ 8.53 (bs, 1H, NH), 8.48 (d, J=5.1 Hz, 1H, ArH), 8.14 (s, 1H, ArH), 7.85 (d, J=75.4 Hz, 1H, ArH), 7.61 (s, 1H, ArH), 7.57 (s, 1H, ArH), 7.42 (d, J=9.0 Hz, 1H, ArH), 7.21 (dd, J=2.4, 2.4 Hz, 1H, ArH), 7.11 (s, 1H, ArH), 3.95 (s, 3H, OCH₃), MS (ESI); m/z 265.0 [M+H]⁺; Anal. Calcd. (C₁₆H₁₂N₂O₂) C, H, N. Molecular weight: 264.09

7-Methoxy-1-quinolin-4-yl-9H-β-carboline 10

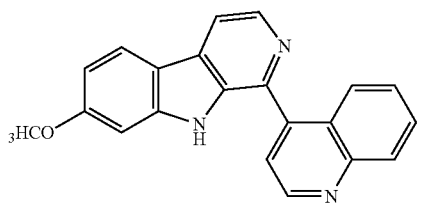

¹H NMR [300 MHz, (CD₃)₂CO]: δ 3.88 (s, 3H), 6.94 (dd, J=2.25 Hz and 8.68 Hz, 1H), 7.00 (d, J=2.25 Hz, 1H), 7.52-7.57 (m, 1H), 7.77 (d, J=4.36 Hz, 1H), 7.79-7.83 (m, 1H), 7.93 (d, J=8.45 Hz, 1H), 8.14 (d, J=5.22 Hz, 1H), 8.18 (d, J=8.34 Hz, 1H), 8.19 (d, J=8.68 Hz, 1H), 8.56 (d, J=5.23 Hz, 1H), 9.01 (d, J=4.36 Hz, 1H),), 10.39 (bs, 1H). Anal. Calculated for (C21H15N3O), (CHN) C, 77.52; H, 4.65; N, 12.91. found C, 77.43; H, 4.61; N, 12.85. MS: m/z 326.2 (MH+). m.pt: 238-239° C. (yield 79%). Molecular weight: 325.12.

6-Methoxy-1-quinolin-4-yl-9H-β-carboline 11

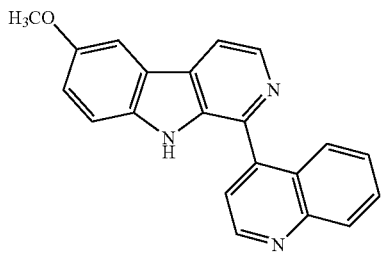 [SMILES: COc1ccc2[nH]c3c(-c4ccnc5ccccc45)nccc3c2c1]

¹H NMR (CDCl₃): δ 9.66 (bs, 1H, NH), 8.76 (d, J=4.5 Hz, 1H, ArH), 8.65 (d, J=5.4 Hz, 1H, ArH), 8.10 (d, J=5.4 Hz, 1H, ArH), 8.04 (d, J=8.7 Hz, 1H, ArH), 7.80 (d, J=8.7 Hz, 1H, ArH), 7.70-7.59 (m, 3H, ArH), 7.51-7.44 (m, 3H, ArH), and 4.00 (s, 3H, OCH₃); MS (ESI); m/z 348.1 [M+Na]⁺; Anal. Calcd. (C₂₁H₁₅N₃O)C, H, N. Molecular weight: 325.12.

1-Isoquinolin-1-yl-7-methoxy-9H-β-carboline 12

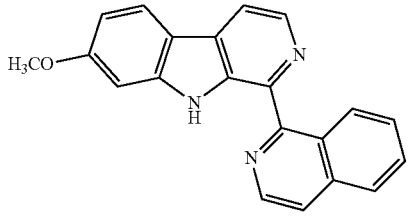

¹H NMR [300 MHz, (CD₃)₂CO]: δ 3.97 (s, 3H), 6.95 (dd, J=2.30 Hz and 8.67 Hz, 1H), 7.43 (d, J=2.25 Hz, 1H), 7.64-7.69 (m, 1H), 7.83-7.89 (m, 1H), 8.05 (d, J=8.03 Hz, 1H), 8.17 (d, J=8.67 Hz, 1H), 8.48-8.56 (m, 4H), 8.96 (d, J=8.71 Hz, 1H), 12.02 (bs, 1H). MS: m/z 326.3 (MH⁺), 348.2 (m+Na). Anal. Calculated for (C21H15N3O), (CHN)C, 77.52; H, 4.65 N, 12.91. found C, 77.74; H, 4.68; N, 13.01. MS: m/z 326.2 (MH⁺), 348.2 (m+Na). m.pt: 196-197° C. (yield 82%). Molecular weight: 325.12.

6-Methoxy-1-quinoxalin-5-yl-9H-β-carboline Cmpd 13

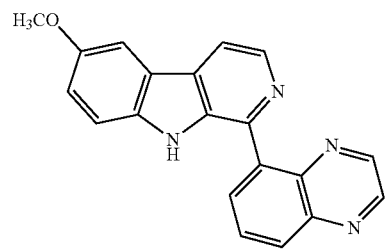 [SMILES: COc1ccc2[nH]c3c(-c4cccc5nccnc45)nccc3c2c1]

¹H NMR (CDCl₃): δ 8.93 (s, 2H, ArH), 8.73 (d, J=1.8 Hz, 2H, ArH), 8.65 (d, J=5.1 Hz, 1H, ArH), 8.56 (dd, J=1.8 and 1.8 Hz, 1H, ArH), 8.00 (d, J=85.4 Hz, 1H, ArH), 7.64 (d, J=2.4 Hz, 1H, ArH), 7.48 (d, J=9.0 Hz, 1H, ArH), 7.27 (s, 1H, ArH), and 3.98 (s, 3H, OCH₃); MS (ESI); m/z 325.1 [M−H]⁻; Anal. Calcd. (C₂₀H₁₄N₄O)C, H, N.

7-Methoxy-1-quinoxalin-5-yl-9H-β-carboline Cmpd 14

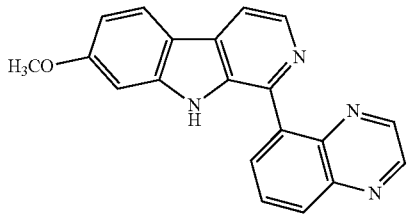

¹H NMR (CDCl₃): δ 11.45 (bs, 1H, NH), 8.90 (d, J=8.7 Hz, 1H, ArH), 8.71 (s, 1H, ArH), 8.54-8.42 (m, 2H, ArH), 8.22 (d, J=8.7 Hz, 1H, ArH), 8.02-7.86 (m, 2H, ArH), 7.10 (s, 1H,

ArH), 6.84 (dd, J=2.4 and 2.4 Hz, 1H, ArH), and 3.81 (s, 3H, OCH₃); MS (ESI); m/z 325.1 [M−H]⁻; Anal. Calcd. (C₂₀H₁₄N₄O)C, H, N.

6-Methoxy-1-quinoxalin-6-yl-9H-β-carboline 13a

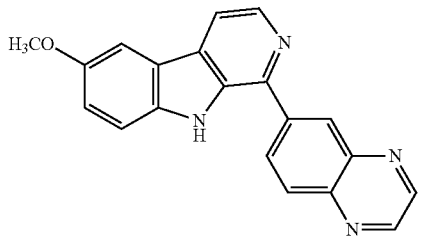 [SMILES: COc1ccc2[nH]c3c(-c4ccc5nccnc5c4)nccc3c2c1]

¹H NMR (CDCl₃): δ 11.45 (bs, 1H, NH), 8.90 (d, J=8.7 Hz, 1H, ArH), 8.71 (s, 1H, ArH), 8.54-8.42 (m, 2H, ArH), 8.22 (d, J=8.7 Hz, 1H, ArH), 8.02-7.86 (m, 2H, ArH), 7.10 (s, 1H, ArH), 6.84 (dd, J=2.4 and 2.4 Hz, 1H, ArH), and 3.81 (s, 3H, OCH₃); MS (ESI); m/z 325.1 [M−H]⁻; Anal. Calcd. (C₂₀H₁₄N₄O)C, H, N. Molecular weight: 326.35.

7-Methoxy-1-quinoxalin-6-yl-9H-β-carboline 14a

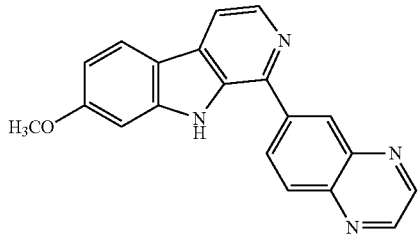 [SMILES: COc1ccc2c(c1)[nH]c1c(-c3ccc4nccnc4c3)nccc12]

¹H NMR (CDCl₃): δ 8.93 (s, 2H, ArH), 8.73 (d, J=1.8 Hz, 2H, ArH), 8.65 (d, J=5.1 Hz, 1H, ArH), 8.56 (dd, J=1.8 and 1.8 Hz, 1H, ArH), 8.00 (d, J=85.4 Hz, 1H, ArH), 7.64 (d, J=2.4 Hz, 1H, ArH), 7.48 (d, J=9.0 Hz, 1H, ArH), 7.27 (s, 1H, ArH), and 3.98 (s, 3H, OCH₃); MS (ESI); m/z 325.1 [M−H]⁻; Anal. Calcd. (C₂₀H₁₄N₄O)C, H, N. Molecular weight: 326.35.

1-Isoquinolin-4-yl-6-methoxy-9H-β-carboline 15

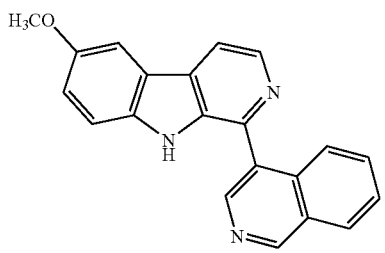

¹H NMR (CDCl₃): δ 10.62 (bs, 1H, NH), 8.82 (s, 1H, ArH), 8.76 (s, 1H, ArH), 8.61 (d, J=4.5 Hz, 1H, ArH), 8.04 (d, J=5.4 Hz, 1H, ArH), 7.96 (d, J=7.5 Hz, 1H, ArH), 7.81-7.60 (m, 4H, ArH), 7.42-7.17 (m, 2H, ArH), and 3.96 (s, 3H, OCH₃); MS (ESI); m/z 324.0 [M−H]⁻; Anal. Calcd. (C₂₁H₁₅N₃O)C, H, N. Molecular weight: 325.12.

1-Isoquinolin-4-yl-7-methoxy-9H-β-carboline 16

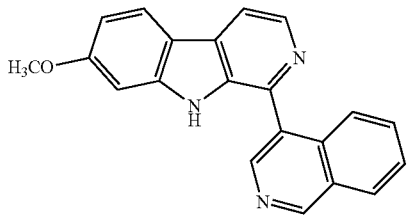

¹H NMR (CDCl₃): δ 11.67 (bs, 1H, NH), 8.78 (s, 1H, ArH), 8.56 (d, J=5.1 Hz, 1H, ArH), 8.49 (s, 1H, ArH), 8.12-7.92 (m, 2H, ArH), 7.79-7.58 (m, 3H, ArH), 7.87-7.96 (m, 2H, ArH), and 3.81 (s, 3H, OCH₃); MS (ESI); m/z 324.1 [M−H]⁻; Anal. Calcd. (C₂₁H₁₅N₃O)C, H, N. Molecular weight: 325.12.

6-Methoxy-1-quinolin-3-yl-9H-β-carboline 17

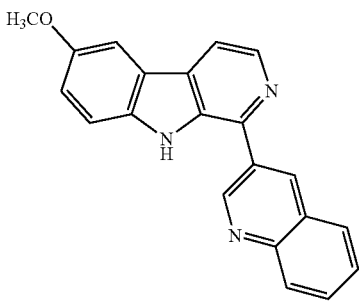 [SMILES: COc1ccc2[nH]c3c(-c4cnc5ccccc5c4)nccc3c2c1]

¹H NMR (DMSO-d6): δ 11.67 (bs, 1H, NH), 9.53 (s, 1H, ArH), 8.97 (s, 1H, ArH), 8.52 (d, J=5.1 Hz, 1H, ArH), 8.27-8.10 (m, 3H, ArH), 7.92-7.80 (m, 2H, ArH), 7.29 (t, J=6.9 Hz, 1H, ArH), 7.58 (d, J=9.0 Hz, 1H, ArH), 7.24 (d, J=9.0 Hz, 1H, ArH), and 3.89 (s, 3H, OCH₃); MS (ESI); m/z 324.0 [M−H]; Anal. Calcd. (C₂₁H₁₅N₃O)C, H, N. Molecular weight: 325.12.

7-Methoxy-1-quinolin-3-yl-9H-β-carboline 18

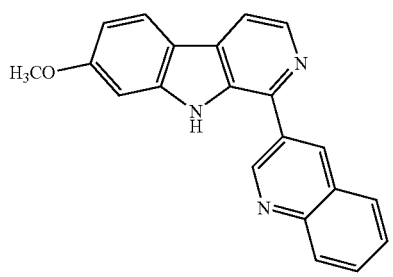 [SMILES: COc1ccc2c(c1)[nH]c1c(-c3cnc4ccccc4c3)nccc12]

¹H NMR (DMSO-d6): δ 9.58 (s, 1H, ArH), 8.82 (s, 1H, ArH), 8.52 (d, J=5.1 Hz, 1H, ArH), 8.16 (d, J=8.4 Hz, 1H, ArH), 8.00 (d, J=8.7 Hz, 1H, ArH), 7.90 (d, J=5.1 Hz, 1H, ArH), 7.29 (t, J=7.2 Hz, 1H, ArH), 7.63 (t, J=7.2 Hz, 1H,

ArH), 7.55 (s, 1H, ArH), 7.07 (s, 1H, ArH), 6.90 (d, J=8.4 Hz, 1H, ArH), and 3.91 (s, 3H, OCH₃); MS (ESI); m/z 324.0 [M−H]; Anal. Calcd. (C₂₁H₁₅N₃O)C, H, N. Molecular weight: 325.12.

6-Methoxy-1-naphthalen-1-yl-9H-β-carboline 19

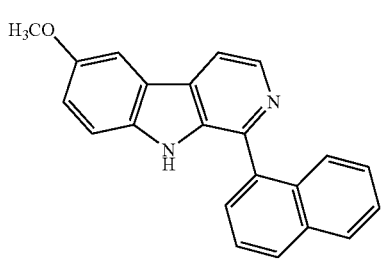 [SMILES: COc1ccc2[nH]c3c(-c4cccc5ccccc45)nccc3c2c1]

¹H NMR (CDCl₃): δ 8.56 (d, J=11.4 Hz, 1H, ArH), 8.21 (bs, 1H, NH), 8.04-7.87 (m, 3H, ArH), 7.81-7.69 (m, 2H, ArH), 7.65-7.37 (m, 4H, ArH), 7.23-7.10 (m, 2H, ArH), and 3.95 (s, 3H, OCH₃); MS (ESI); m/z 323.0 [M−H]⁻; Anal. Calcd. (C₂₂H₁₆N₂O)C, H, N. Molecular weight: 324.13.

7-Methoxy-1-naphthalen-1-yl-9H-β-carboline 20

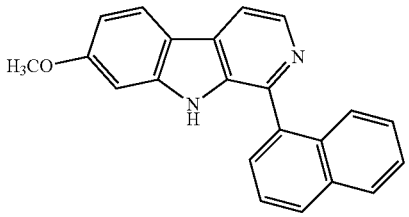

¹H NMR (CDCl₃): δ 8.58 (d, J=5.4 Hz, 1H, ArH), 8.09 (bs, 1H, NH), 8.07-7.90 (m, 4H, ArH), 7.76 (t, J=8.4 Hz, 2H, ArH), 7.65-7.40 (m, 3H, ArH), 6.92 (d, J=8.7 Hz, 1H, ArH), 6.76 (s, 1H, ArH), and 3.83 (s, 3H, OCH₃); MS (ESI); m/z 323.0 [M−H]⁻; Anal. Calcd. (C₂₂H₁₆N₂O)C, H, N. Molecular weight: 324.13.

6-Methoxy-1-quinolin-5-yl-9H-β-carboline 21

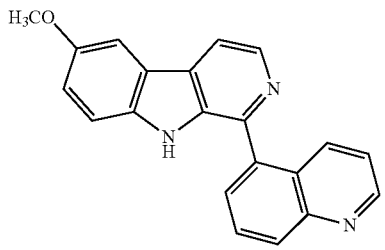 [SMILES: COc1ccc2[nH]c3c(-c4cccc5ncccc45)nccc3c2c1]

¹H NMR (DMSO-d6): δ 11.00 (bs, 1H, NH), 8.94 (s, 1H, ArH), 8.48 (d, J=5.1 Hz, 1H, ArH), 8.19 (d, J=8.7 Hz, 2H, ArH), 8.05-7.85 (m, 3H, ArH), 7.53-7.38 (m, 2H, ArH), 7.16 (d, J=8.7 Hz, 1H, ArH), and 3.88 (s, 3H, OCH₃); MS (ESI); m/z 324.0 [M−H]; Anal. Calcd. (C₂₁H₁₅N₃O) C, H, N. Molecular weight: 325.12.

7-Methoxy-1-quinolin-5-yl-9H-β-carboline 22

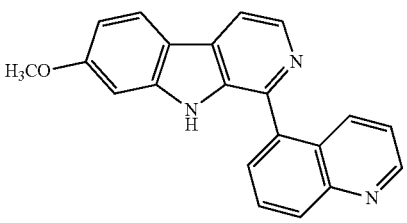 [SMILES: COc1ccc2c(c1)[nH]c1c(-c3cccc4ncccc34)nccc12]

¹H NMR (DMSO-d6): δ 8.97 (s, 1H, ArH), 8.60 (d, J=5.4 Hz, 1H, ArH), 8.30-8.20 (m, 2H, ArH), 8.06 (d, J=8.7 Hz, 2H, ArH), 8.00-7.90 (m, 2H, ArH), 7.32 (dd, J=4.2 and 4.2 Hz, 1H, ArH), 6.96 (s, 1H, ArH), 6.89 (dd, J=2.1 and 2.1 Hz, 1H, ArH), and 3.90 (s, 3H, OCH₃); MS (ESI); m/z 324.0 [M−H]; Anal. Calcd. (C₂₁H₁₅N₃O)C, H, N. Molecular weight: 325.12.

1-Isoquinolin-5-yl-6-methoxy-9H-β-carboline 23

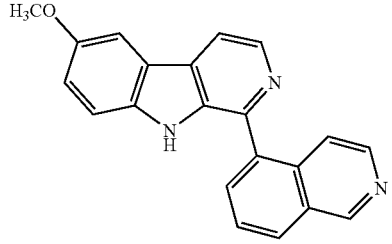 [SMILES: COc1ccc2[nH]c3c(-c4cccc5cnccc45)nccc3c2c1]

¹H NMR (CDCl₃): δ 9.65 (bs, 1H, NH), 8.85 (s, 1H, ArH), 8.56 (d, J=5.4 Hz, 1H, ArH), 8.24 (d, J=6.0 Hz, 1H, ArH), 8.05-7.85 (m, 3H, ArH), 7.75-7.63 (m, 3H, ArH), 7.49 (d, J=6.0 Hz, 1H, ArH), 7.35 (d, J=9.0 Hz, 1H, ArH), 7.18 (dd, J=2.4 and 2.4 Hz, 1H, ArH), and 3.96 (s, 3H, OCH₃); MS (ESI); m/z 323.9[M−H]; Anal. Calcd. (C₂₁H₁₅N₃O)C, H, N. Molecular weight: 325.12.

1-Isoquinolin-5-yl-7-methoxy-9H-β-carboline 24

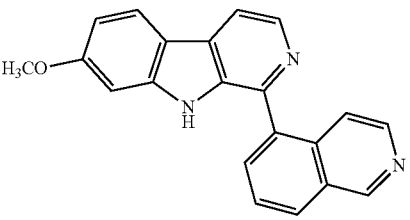 [SMILES: COc1ccc2c(c1)[nH]c1c(-c3cccc4cnccc34)nccc12]

¹H NMR (CDCl₃): δ 9.20 (s, 1H, ArH), 8.62 (d, J=5.4 Hz, 1H, ArH), 8.53 (bs, 1H, NH), 8.42 (d, J=6.0 Hz, 1H, ArH), 8.20-8.03 (m, 3H, ArH), 7.80 (t, J=8.1 Hz, 1H, ArH), 7.62 (d, J=6.0 Hz, 1H, ArH), 6.96 (dd, J=2.4 and 2.4 Hz, 1H, ArH), 6.89 (s, 1H, ArH), and 3.88 (s, 3H, OCH₃); MS (ESI); m/z 323.9[M−H]; Anal. Calcd. (C₂₁H₁₅N₃O)C, H, N. Molecular weight: 325.12.

6-Methoxy-1-naphthalen-2-yl-9H-β-carboline 25

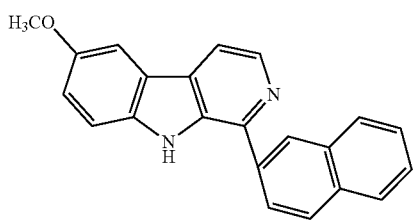 [SMILES: COc1ccc2[nH]c3c(-c4ccc5ccccc5c4)nccc3c2c1]

¹H NMR (CDCl₃ and DMSO-d6): δ 8.58-8.43 (m, 2H, ArH), 8.14 (d, J=8.4 Hz, 1H, ArH), 8.06-7.885 (m, 4H, ArH), 7.64-7.46 (m, 4H, ArH), 8.16 (d, J=8.1 Hz, 1H, ArH), and 3.92 (s, 3H, OCH₃); MS (ESI); m/z 323.1 [M−H]⁻; Anal. Calcd. (C₂₂H₁₆N₂O)C, H, N. Molecular weight: 324.13.

7-Methoxy-1-naphthalen-2-yl-9H-β-carboline 26

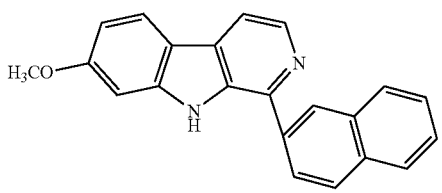 [SMILES: COc1ccc2c(c1)[nH]c1c(-c3ccc4ccccc4c3)nccc12]

¹H NMR (CDCl₃): δ 8.78 (bs, 1H, NH), 8.56 (d, J=5.4 Hz, 1H, ArH), 8.35 (s, 1H, ArH), 8.12-7.97 (m, 3H, ArH), 7.96-7.83 (m, 3H, ArH), 7.60-7.48 (m, 2H, ArH), 6.96 (s, 1H, ArH), and 3.90 (s, 3H, OCH₃); MS (ESI); m/z 323.2 [M−H]⁻; Anal. Calcd. (C₂₂H₁₆N₂O)C, H, N. Molecular weight: 324.13.

1-Anthracen-9-yl-6-methoxy-9H-β-carboline 27

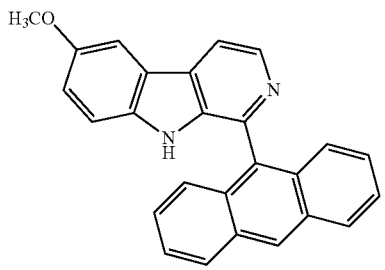 [SMILES: COc1ccc2[nH]c3c(-c4c5ccccc5cc5ccccc45)nccc3c2c1]

¹H NMR (CDCl₃): δ 8.72 (d, J=5.1 Hz, 1H, ArH), 8.64 (s, 1H, NH), 8.20-8.08 (m, 3H, ArH), 7.68 (s, 1H, ArH), 7.62 (s, 1H, ArH), 7.53-7.45 (m, 3H, ArH), 7.39-7.27 (m, 2H, ArH), 7.13 (s, 2H, ArH), and 3.97 (s, 3H, OCH₃); MS (ESI); m/z 373.0 [M−H]⁻; Anal. Calcd. (C₂₆H₁₈N₂O)C, H, N. Molecular weight: 374.14.

1-Anthracen-9-yl-7-methoxy-9H-β-carboline 28

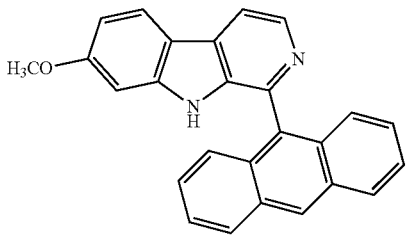 [SMILES: COc1ccc2c(c1)[nH]c1c(-c3c4ccccc4cc4ccccc34)nccc12]

¹H NMR (CDCl₃): δ 9.49 (s, 1H, NH), 8.70-8.59 (m, 2H, ArH), 8.15-8.00 (m, 4H, ArH), 7.55-7.40 (m, 4H, ArH), 7.30 (d, J=7.8 Hz, 2H, ArH), 6.77 (dd, J=2.1 and 2.1 Hz, 1H, ArH), 6.78 (s, 3H, ArH), and 3.79 (s, 3H, OCH₃); MS (ESI); m/z 373.1 [M−H]⁻; Anal. Calcd. (C₂₆H₁₈N₂O)C, H, N. Molecular weight: 374.14.

6-Methoxy-1-phenanthren-9-yl-9H-β-carboline 29

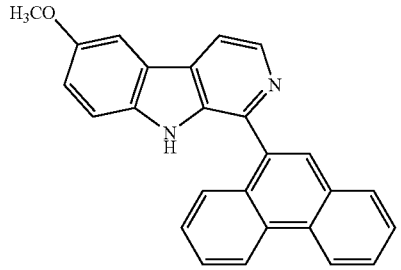 [SMILES: COc1ccc2[nH]c3c(-c4cc5ccccc5c5ccccc45)nccc3c2c1]

¹H NMR (CDCl₃): δ 8.79 (t, J=8.7 Hz, 2H, ArH), 8.55 (d, J=5.1 Hz, 1H, ArH), 8.05-7.94 (m, 3H, ArH), 7.81 (d, J=8.1 Hz, 1H, ArH), 7.76-7.61 (m, 4H, ArH), 7.49 (t, J=7.8 Hz, 2H, ArH), 7.36 (d, J=8.7 Hz, 1H, ArH), 7.13 (dd, J=2.4 and 2.4 Hz, 1H, ArH), and 3.93 (s, 3H, OCH₃); MS (ESI); m/z 373.0 [M−H]⁻; Anal. Calcd. (C₂₆H₁₈N₂O)C, H, N. Molecular weight: 374.14.

7-Methoxy-1-phenanthren-9-yl-9H-β-carboline 30

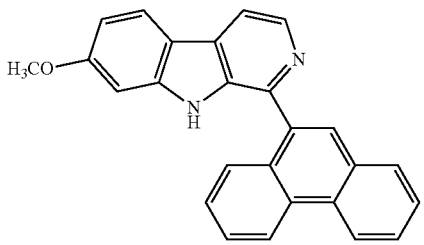 [SMILES: COc1ccc2c(c1)[nH]c1c(-c3cc4ccccc4c4ccccc34)nccc12]

¹H NMR (CDCl₃): δ 8.80 (d, J=8.1 Hz, 1H, ArH), 8.75 (d, J=8.1 Hz, H, ArH), 8.58 (d, J=5.4 Hz, 1H, ArH), 8.17 (s, 1H, NH), 8.08-7.88 (m, 4H, ArH), 7.82-7.60 (m, 4H, ArH), 7.50 (t, J=7.8 Hz, 2H, ArH), 6.92 (dd, J=2.1 and 2.1 Hz, 1H, ArH), 6.73 (s, 1H, ArH), and 3.80 (s, 3H, OCH₃); MS (ESI); m/z 373.0 [M−H]⁻; Anal. Calcd. (C₂₆H₁₈N₂O)C, H, N. Molecular weight: 374.14.

6-Methoxy-1-phenyl-9H-β-carboline 31

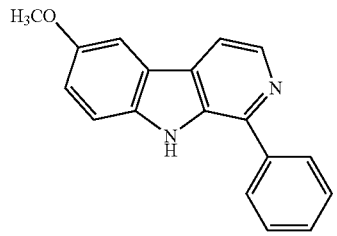 [SMILES: COc1ccc2[nH]c3c(-c4ccccc4)nccc3c2c1]

¹H NMR (CDCl₃): δ 8.81 (bs, 1H, NH), 8.52 (d, J=5.4 Hz, 1H, ArH), 7.97-7.86 (m, 3H, ArH), 7.58 (s, 1H, ArH), 7.55-7.32 (m, 4H, ArH), 7.19 (d, J=9.0 Hz, 1H, ArH), and 3.94 (s, 3H, OCH₃); MS (ESI); m/z 273.0 [M−H]⁻; Anal. Calcd. (C₁₈H₁₄N₂O)C, H, N. Molecular weight: 274.11.

7-Methoxy-1-phenyl-9H-β-carboline 32

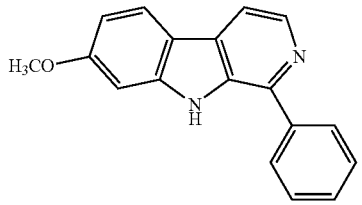 [SMILES: COc1ccc2c(c1)[nH]c1c(-c3ccccc3)nccc12]

¹H NMR (CDCl₃): δ 8.54 (d, J=5.4 Hz, 2H, ArH), 8.06-7.93 (m, 3H, ArH), 7.84 (d, J=5.1 Hz, 1H, ArH), 7.58 (t, J=7.8 Hz, 2H, ArH), 7.48 (t, J=7.6 Hz, 1H, ArH), 6.97-6.92 (m, 2H, ArH), and 3.91 (s, 3H, OCH₃); MS (ESI); m/z 273.0 [M−H]⁻; Anal. Calcd. (C₁₈H₁₄N₂O)C, H, N. Molecular weight: 274.11.

6-Methoxy-1-(2-methyl-naphthalen-1-yl)-9H-β-carboline 33

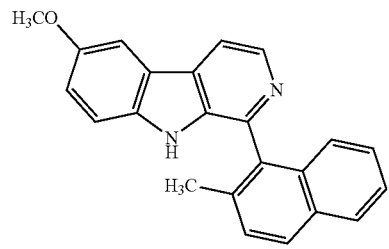 [SMILES: COc1ccc2[nH]c3c(-c4c(C)ccc5ccccc45)nccc3c2c1]

¹H NMR (CDCl₃): δ 8.59 (d, J=5.4 Hz, 1H, ArH), 7.80 (d, J=5.4 Hz, 1H, ArH), 8.91 (d, J=8.4 Hz, 2H, ArH), 7.82 (bs, 1H, NH), 7.65 (s, 1H, ArH), 7.54-7.40 (m, 2H, ArH), 7.34-

7.12 (m, 4H, ArH), and 3.96 (s, 3H, OCH₃); MS (ESI); m/z 339.2 [M+H]⁺⁻; Anal. Calcd. (C₂₃H₁₈N₂O)C, H, N. Molecular weight: 338.14.

7-Methoxy-1-(2-methyl-naphthalen-1-yl)-9H-β-carboline 34

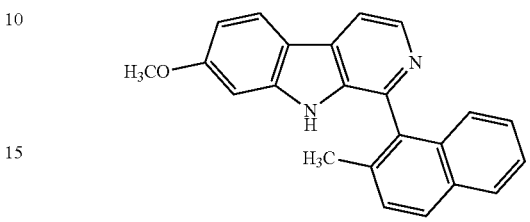

¹H NMR (CDCl₃): δ 8.53 (d, J=5.4 Hz, 1H, ArH), 7.05 (d, J=5.4 Hz, 1H, ArH), 8.01 (bs, 1H, NH), 7.94-7.85 (m, 3H, ArH), 7.51-7.37 (m, 2H, ArH), 7.31-7.21 (m, 2H, ArH), 6.90 (dd, J=2.4 and 2.4 Hz, 1H, ArH), 6.65 (s, 1H, ArH), and 3.75 (s, 3H, OCH₃); MS (ESI); m/z 339.2 [M+H]⁺⁻; Anal. Calcd. (C₂₃H₁₈N₂O)C, H, N. Molecular weight: 338.14.

6-Methoxy-1-(6-methoxy-naphthalen-1-yl)-9H-β-carboline 35

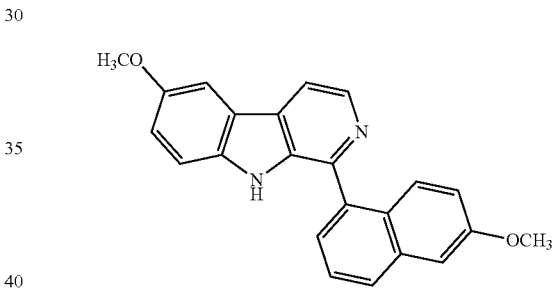

¹H NMR (CDCl₃): δ 8.69 (bs, 1H, NH), 8.57 (d, J=5.4 Hz, 1H, ArH), 8.31 (s, 1H, ArH), 8.05 (dd, J=1.5 and 1.5 Hz, 1H, ArH), 7.92-7.79 (m, 3H, ArH), 7.61 (s, 1H, ArH), 7.43 (d, J=9.0 Hz, 1H, ArH), 7.30-7.15 (m, 3H, ArH), 3.97 (s, 3H, OCH₃), and 3.96 (s, 3H, OCH₃); MS (ESI); m/z 353.0 [M−H]⁻; Anal. Calcd. (C₂₃H₁₈N₂O₂) C, H, N. Molecular weight: 354.14.

6-Benzyloxy-1-naphthalen-1-yl-9H-β-carboline 36

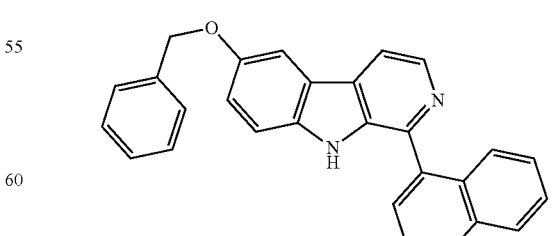

¹H NMR (CDCl₃): δ 8.59 (d, J=5.4 Hz, 1H, ArH), 8.10-7.96 (m, 4H, ArH), 7.81-7.71 (m, 3H, ArH), 7.65-7.54 (m, 4H, ArH), 7.48-7.35 (m, 4H, ArH), 7.23 (s, 1H, ArH), and 5.22 (s, 2H, OCH$_2$); MS (ESI); m/z 401.0 [M+H]$^{+-}$; Anal. Calcd. (C$_{28}$H$_{20}$N$_2$O)C, H, N. Molecular weight: 400.

8-Methyl-1-naphthalen-1-yl-9H-β-carboline 37

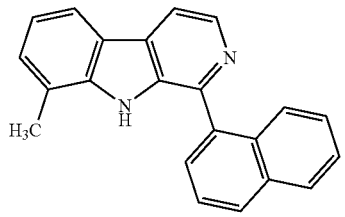 [SMILES: Cc1cccc2c1[nH]c1c(-c3cccc4ccccc34)nccc12]

$^1$H NMR (CDCl$_3$): δ 8.67 (d, J=5.1 Hz, 1H, ArH), 8.12-7.98 (m, 3H, ArH), 7.86-7.67 (m, 3H, ArH), 7.57 (t, J=6.9 Hz, 1H, ArH), 7.45 (t, J=6.9 Hz, 1H, ArH), 7.36 (d, J=7.2 Hz, 1H, ArH), 7.30-7.25 (m, 2H, ArH), and 2.43 (s, 3H, CH$_3$); MS (ESI); m/z 307.1 [M–H]$^-$; Anal. Calcd. (C$_{22}$H$_{16}$N$_2$) C, H, N. Molecular weight: 308.13.

6-Methoxy-1-(4-pyridin-2-yl-phenyl)-9H-β-carboline 38

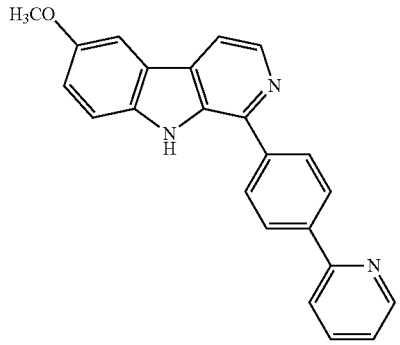 [SMILES: COc1ccc2[nH]c3c(-c4ccc(-c5ccccn5)cc4)nccc3c2c1]

$^1$H NMR (CDCl$_3$): δ 9.21 (bs, 1H, NH), 8.70 (s, 1H, ArH), 8.52 (d, J=5.1 Hz, 1H, ArH), 8.10-7.86 (m, 5H, ArH), 7.78-7.54 (m, 3H, ArH), 7.40 (d, J=8.7 Hz, 1H, ArH), 7.30-7.15 (m, 2H, ArH), and 3.94 (s, 3H, OCH$_3$); MS (ESI); m/z 352.3[M+H]; Anal. Calcd. (C$_{23}$H$_{17}$N$_3$O)C, H, N. Molecular weight: 351.14.

8-methoxy-1-(naphthalen-1-yl)-9H-pyrido[3,4-b]indole 39

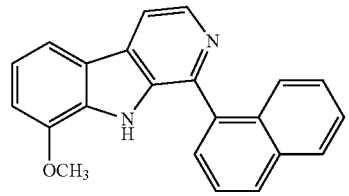 [SMILES: COc1cccc2c1[nH]c1c(-c3cccc4ccccc34)nccc12]

Yield 28%; $^1$H NMR (CDCl$_3$): δ 8.63 (d, J=5.0 Hz, 1H, ArH), 8.13 (s, 1H, ArH), 8.08-7.97 (m, 2H, ArH), 7.83-7.64 (m, 3H, ArH), 7.59-7.51 (m, 2H, ArH), 7.48-7.40 (m, 1H, ArH), 7.27-7.21 (m, $^1$H, ArH), 6.98 (d, J=6.0 Hz, 1H, ArH), and 3.90 (s, 3H, CH$_3$); MS (ESI); m/z 325.1 [M+H]$^+$; Anal. Calcd. (C$_{22}$H$_{16}$N$_2$O)C, H, N.

1-(naphthalen-1-yl)-9H-pyrido[3,4-b]indol-6-ol 40

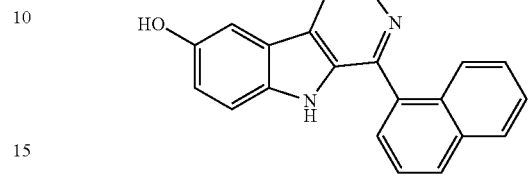

Yield 26%; $^1$H NMR (CDCl$_3$): δ 8.64 (d, J=6.0 Hz, 1H, ArH), 8.08-7.94 (m, 2H, ArH), 7.86-7.75 (m, 2H, ArH), 7.70-7.42 (m, 5H, ArH), 7.25 (d, J=9.0 Hz, 1H, ArH), and 7.10 (d, J=9.0 Hz, 1H, ArH); MS (ESI); m/z 311.1 [M+H]$^+$; Anal. Calcd. (C$_{21}$H$_{14}$N$_2$O)C, H, N.

6-methoxy-1-(naphthalen-1-yl)-4-phenyl-9H-pyrido[3,4-b]indole 41

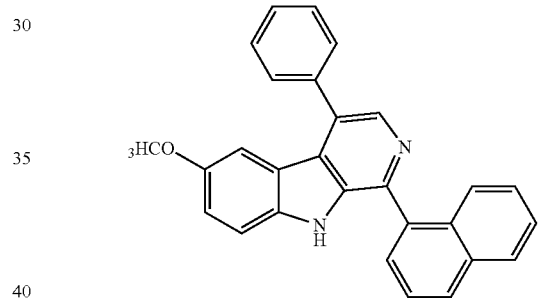

Yield 35%; $^1$H NMR (CDCl$_3$): δ 8.52 (s, 1H, ArH), 8.08-7.78 (m, 5H, ArH), 7.74-7.45 (m, 6H, ArH), 7.38-7.33 (m, 2H, ArH), 7.08-7.22 (m, 2H, ArH), and 3.7 (s, 3H, CH$_3$); MS (ESI); m/z 401.1 [M+H]$^+$; Anal. Calcd. (C$_{28}$H$_{20}$N$_2$O)C, H, N.

N-methyl-1-(1-(naphthalen-1-yl)-9H-pyrido[3,4-b]indol-6-yl)methanesulfonamide 42

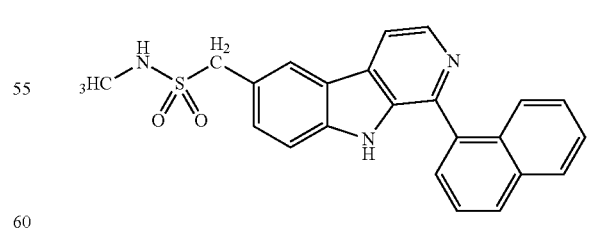

Yield 24%; $^1$H NMR (CDCl$_3$): δ 8.70 (d, J=5.5 Hz, 1H, ArH), 8.23 (s, 1H, ArH), 8.05-7.98 (m, 3H, ArH), 7.79 (d, J=5.5 Hz, 1H, ArH), 7.74 (d, J=8.5 Hz, 1H, ArH), 7.68-7.65 (m, 1H, ArH), 7.56-7.53 (m, 2H, ArH), 7.46-7.38 (m, 2H, ArH), 4.45 (s, 2H, CH$_2$) and 2.76 (d, J=5.5 Hz, 3H, CH$_3$); MS (ESI); m/z 402.1 [M7.46-7.38 (m, 2H, ArH), 4.45 (s, 2H, CH$_2$) and 2.76 (d, J=5.5 Hz, 3H, CH$_3$); MS (ESI); m/z 402.1 [M+H]$^+$; Anal. Calcd. (C$_{23}$H$_{19}$N$_3$O$_2$S)C, H, N.

5-methyl-1-(naphthalen-1-yl)-9H-pyrido[3,4-b]indole 43

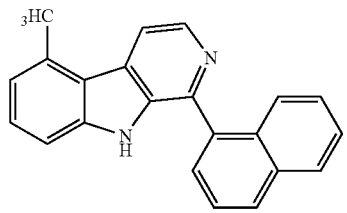

Yield 26%; $^1$H NMR (CDCl$_3$): δ 8.67 (d, J=5.6 Hz, 1H, ArH), 8.12 (d, J=5.6 Hz, 1H, ArH), 8.03-7.98 (m, 2H, ArH), 7.79 (d, J=7.2 Hz, 1H, ArH), 7.74 (d, J=8.4 Hz, 1H, ArH), 7.68-7.64 (m, 1H, ArH), 7.56-7.52 (m, 2H, ArH), 7.43-7.39 (m, 2H, ArH), 7.22 (d, J=8.0 Hz, 1H, ArH), 7.09 (d, J=7.6 Hz, 1H, ArH) and 2.95 (s, 3H, CH$_3$); MS (ESI); m/z 309.1 [M+H]$^+$; Anal. Calcd. (C$_{22}$H$_{16}$N$_2$) C, H, N.

1-(5-fluoronaphthalen-1-yl)-6-methoxy-9H-pyrido[3,4-b]indole 44

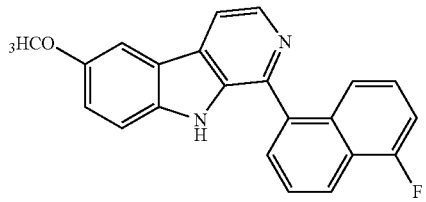

Yield 28%; $^1$H NMR (CDCl$_3$): δ 8.64 (d, J=5.4 Hz, 1H, ArH), 8.32 (d, J=8.7 Hz, 1H, ArH), 8.02 (d, J=5.4 Hz, 1H, ArH), 7.90-7.82 (m, 2H, ArH), 7.76-7.55 (m, 3H, ArH), 7.43-7.18 (m, 3H, ArH), and 3.98 (s, 3H, OCH$_3$); MS (ESI); m/z 340.9 [M−H]−; Anal. Calcd. (C$_{22}$H$_{15}$FN$_2$O) C, H, N.

1-(5-bromonaphthalen-1-yl)-6-methoxy-9H-pyrido[3,4-b]indole 45

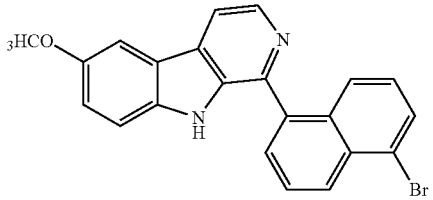

Yield—%; $^1$H NMR (CDCl$_3$): δ 8.60 (d, J=5.6 Hz, 1H, ArH), 8.44 (d, J=5.0 Hz, 1H, ArH), 7.01 (d, J=5.0 Hz, 1H, ArH), 7.87-7.71 (m, 3H, ArH), 7.63 (s, 1H, ArH), 7.28-7.16 (m, 3H, ArH), and 3.98 (s, 3H, CH$_3$); MS (ESI); m/z 403.1 and 404.1 (bromo pattern) [M+H]+; Anal. Calcd. (C$_{22}$H$_{15}$BrN$_2$O)C, H, N.

1-(5-bromonaphthalen-1-yl)-6-methyl-9H-pyrido[3,4-b]indole 46

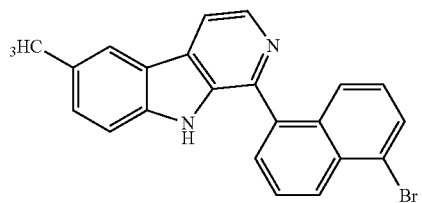

Yield 24%; $^1$H NMR (CDCl$_3$): δ 8.64 (d, J=5.0 Hz, 1H, ArH), 8.45 (d, J=8.5 Hz, 1H, ArH), 8.02-7.98 (m, 2H, ArH), 7.85-7.72 (m, 3H, ArH), 7.57 (t, J=6.9 Hz, 1H, ArH), 7.56-7.53 (m, 1H, ArH), 7.36 (d, J=8.0 Hz, 1H, ArH), 7.28-7.24 (m, 2H, ArH), and 2.58 (s, 3H, CH$_3$); MS (ESI); m/z 384.6 and 385.6 (bromo pattern) [M−H]−; Anal. Calcd. (C$_{22}$H$_{15}$BrN$_2$) C, H, N.

1-(1,2-Dihydroacenaphthalen-5-yl)-6-methoxy-9H-pyrido[3,4-b]indole 47

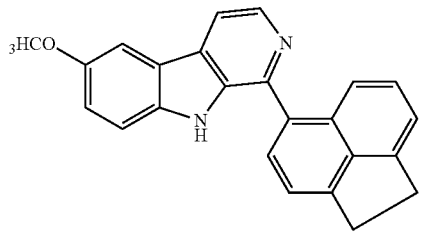

Yield 23%; $^1$H NMR (CDCl$_3$): δ 8.60 (d, J=5.0 Hz, 1H, ArH), 8.01 (bs, 1H, NH), 7.95 (d, J=5.5 Hz, 1H, ArH), 7.79 (d, J=7.5 Hz, 1H, ArH), 7.61 (s, 1H, ArH), 7.56 (d, J=8.5 Hz, 1H, ArH), 7.45-7.39 (m, 2H, ArH), 7.34 (d, J=6.5 Hz, 1H, ArH), 7.25 (s, 1H, ArH), 7.15 (d, J=9.0 Hz, 1H, ArH), 3.94 (s, 3H, OCH$_3$), and 3.48 (s, 4H, CH$_2$); MS (ESI); m/z 350.41 [M+H]+; Anal. Calcd. (C$_{24}$H$_{18}$N$_2$O)C, H, N.

6-Chloro-1-(naphthalen-1-yl)benzo[4,5]thieno[2,3-c]pyridine 48

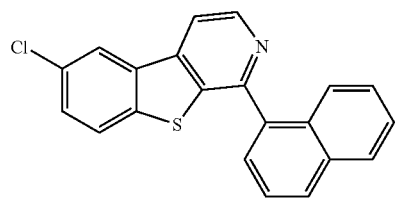 [SMILES: Clc1ccc2sc3c(-c4cccc5ccccc45)nccc3c2c1]

Yield 32%; $^1$H NMR (CDCl$_3$): δ 8.87 (d, J=5.5 Hz, 1H, ArH), 8.26 (s, 1H, ArH), 8.04-7.99 (m, 2H, ArH), 7.95 (d, J=8.5 Hz, 1H, ArH), 7.81-7.71 (m, 3H, ArH), 7.61 (t, J=8.0

Hz, 1H, ArH), 7.52 (t, J=7.0 Hz, 2H, ArH) and 7.42 (t, J=8.0 Hz, 1H, ArH); MS (ESI); m/z 346.1 [M+H]+; Anal. Calcd. ($C_{21}H_{12}ClNS$)C, H, N.

1-(naphthalen-1-yl)benzofuro[2,3-c]pyridine 49

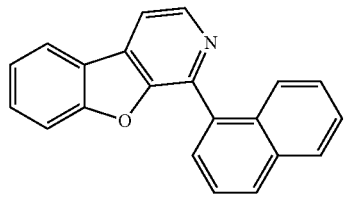 [SMILES: c1ccc2c(-c3nccc4c3oc3ccccc34)cccc2c1]

Yield 22%; $^1$H NMR (CDCl$_3$): δ 8.77 (d, J=5.0 Hz, 1H, ArH), 8.10 (d, J=7.5 Hz, 1H, ArH), 8.02 (d, J=8.5 Hz, 1H, ArH), 7.96 (d, J=5.0 Hz, 2H, ArH), 7.91 (d, J=8.5 Hz, 1H, ArH), 7.86 (d, J=6.5 Hz, 1H, ArH), 7.65 (t, J=8.0 Hz, 1H, ArH), 7.62-7.50 (m, 3H, ArH), and 7.44 (t, J=8.0 Hz, 2H, ArH); MS (ESI); m/z 296.7 [M+H]+; Anal. Calcd. ($C_{21}H_{13}NO$) C, H, N.

1-(Naphthalen-1-yl)benzo[4,5]thieno[2,3-c]pyridine 50

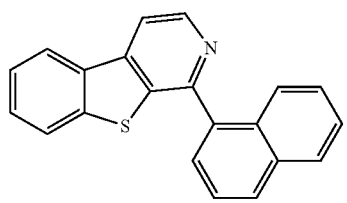 [SMILES: c1ccc2c(-c3nccc4c3sc3ccccc34)cccc2c1]

Yield 31%; $^1$H NMR (CDCl$_3$): δ 8.83 (d, J=5.5 Hz, 1H, ArH), 8.27 (d, J=7.0 Hz, 1H, ArH), 8.04 (d, J=5.5 Hz, 1H, ArH), 7.99 (d, J=8.5 Hz, 1H, ArH), 7.94 (d, J=8.0 Hz, 1H, ArH), 7.79 (t, J=8.0 Hz, 3H, ArH), 7.60 (t, J=7.5 Hz, 1H, ArH), 7.58-7.48 (m, 3H, ArH), and 7.40 (t, J=7.5 Hz, 1H, ArH); MS (ESI); m/z 312.4 [M+H]+; Anal. Calcd. ($C_{21}H_{13}NS$)C, H, N.

6-Methyl-1-(naphthalen-1-yl)-9H-pyrido[3,4-b]indole 51

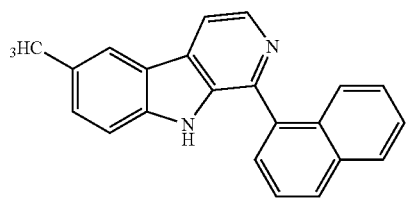

Yield 21%; $^1$H NMR (CDCl$_3$): δ 8.60 (d, J=4.8 Hz, 1H, ArH), 8.23 (d, J=7.6 Hz, 1H, ArH), 8.10-7.91 (m, 3H, ArH), 7.70-7.54 (m, 3H, ArH), 7.52-7.27 (m, 5H, ArH), and 3.10 (s, 3H, NCH$_3$); MS (ESI); m/z 309.1 [M+H]+; Anal. Calcd. ($C_{22}H_{16}N_2$) C, H, N.

1-(Naphthalen-1-yl)-6-(trifluoromethoxy)-9H-pyrido[3,4-b]indole 52

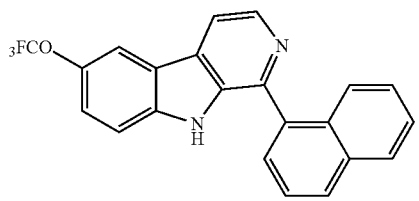

Yield 34%; $^1$H NMR (CDCl$_3$): δ 8.62 (d, J=5.2 Hz, 1H, ArH), 8.34 (s, 1H, ArH), 8.10-7.92 (m, 3H, ArH), 7.73 (d, J=7.4 Hz, 2H, ArH) and 7.65-7.25 (m, 5H, ArH); MS (ESI); m/z 379.9 [M+H]+; Anal. Calcd. ($C_{22}H_{13}F_3N_2O$)C, H,N.

1-(Naphthalen-1-yl)-9H-pyrido[3,4-b]indole-6-carbonitrile 53

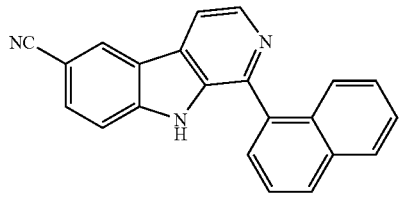 [SMILES: N#Cc1ccc2[nH]c3c(-c4cccc5ccccc45)nccc3c2c1]

Yield 32%; $^1$H NMR (CDCl$_3$): δ 8.77 (d, J=6.0 Hz, 1H, ArH), 8.56 (s, 1H, ArH), 7.90-7.82 (m, 2H, ArH), 8.09-8.00 (m, 3H, ArH), 7.80-7.73 (m, 3H, ArH), 7.57-7.53 (m, 2H, ArH), and 7.48-7.44 (m, 2H, ArH); MS (ESI); m/z 321.1 [M+H]+; Anal. Calcd. ($C_{22}H_{13}N_3$) C, H, N.

6-Bromo-1-(naphthalen-1-yl)-9H-pyrido[3,4-b]indole 54

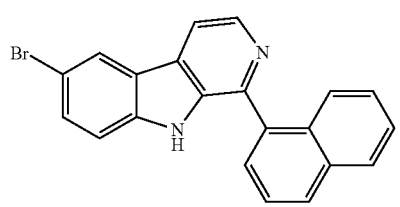

Yield 35%; $^1$H NMR (CDCl$_3$): δ 8.85 (d, J=5.0 Hz, 1H, ArH), 8.40 (s, 1H, ArH), 8.04-7.92 (m, 3H, ArH), 7.82-7.74 (m, 2H, ArH), 7.68-7.48 (m, 3H, ArH), 7.41 (t, J=8.0 Hz, 1H, ArH), and 3.95 (s, 3H, OCH₃); MS (ESI); m/z 390.1 and 392.0 (bromo pattern) [M+H]+; Anal. Calcd. ($C_{21}H_{13}BrN_2$) C, H, N.

Ethyl-6-methoxy-1-(naphthalen-1-yl)-9H-pyrido[3,4-b]indole-3-carboxylate 55

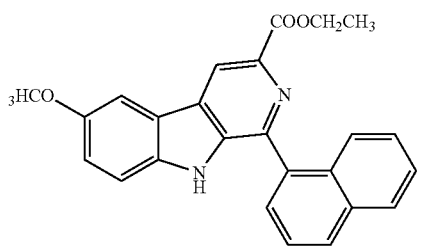

Yield 25%; ¹H NMR (CDCl₃): δ 8.92 (s, 1H, NH), 8.14 (s, 1H, ArH), 8.10-7.93 (m, 2H, ArH), 7.78-7.58 (m, 3H, ArH), 7.54-7.36 (m, 3H, ArH), 7.30-7.24 (m, 2H, ArH), 7.18 (d, J=9.0 Hz, 1H, ArH), 4.50 (q, J=7.0 Hz, 2H, OCH₂), 3.96 (s, 3H, OCH₃), and 1.46 (t, J=7.0 Hz, 3H, CH₃); MS (ESI); m/z 397.3 [M+H]+; Anal. Calcd. ($C_{25}H_{20}N_2O_3$) C, H, N.

9-Methyl-1-(naphthalen-1-yl)-9H-pyrido[3,4-b]indole 56

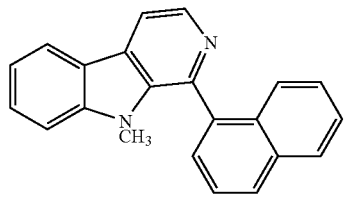 [SMILES: Cn1c2ccccc2c2ccnc(-c3cccc4ccccc34)c21]

Yield 21%; ¹H NMR (CDCl₃): δ 8.60 (d, J=4.8 Hz, 1H, ArH), 8.23 (d, J=7.6 Hz, 1H, ArH), 8.10-7.91 (m, 3H, ArH), 7.70-7.54 (m, 3H, ArH), 7.52-7.27 (m, 5H, ArH), and 3.10 (s, 3H, NCH₃); MS (ESI); m/z 309.1 [M+H]+; Anal. Calcd. ($C_{22}H_{16}N_2$) C, H, N.

6-Methoxy-9-methyl-1-(naphthalen-1-yl)-9H-pyrido[3,4-b]indole 57

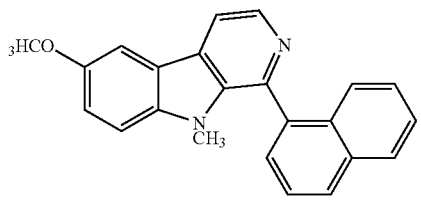

Yield 29%; ¹H NMR (CDCl₃): δ 8.56 (d, J=5.2 Hz, 1H, ArH), 8.05-7.30 (m, 3H, ArH), 7.69-7.59 (m, 3H, ArH), 7.48 (t, J=7.2 Hz, 1H, ArH), 7.40-7.31 (m, 2H, ArH), 7.27-7.20 (m, 2H, ArH), 3.97 (s, 3H, OCH₃), and 3.07 (s, 3H, NCH₃); MS (ESI); m/z 339.3 [M+H]⁺; Anal. Calcd. ($C_{23}H_{18}N_2O$) C, H, N.

EXAMPLE 3

In vitro Antiproliferative Activity of Substituted β-carbolines and Analogs

Substituted β-carboline compounds 4 to 38 were tested for antiproliferative activity against HCT116 colon cancer cells and HPAC, Mia-PaCa2 and Panc-1 pancreatic cancer cell lines. Table 1 lists the IC50 values for the substituted β-carbolines. Compounds 11, 19, 25, 29, 30, and 36 demonstrated significantly lower IC50 values.

TABLE 1

| Cmpd | HCT116 IC50 (μM) | HCT116 P53 −/− IC50 (μM) | HPAC IC50 (μM) | Mia-PaCa2 IC50 (μM) | Panc-1 IC50 (μM) |
|---|---|---|---|---|---|
| 4 | — | | 21.64 | 12.52 | >50.00 |
| 5 | — | | >50.00 | 44.83 | >50.00 |
| 10 | 7.00 | 18.7 | | | |
| 11 | 0.51 | 0.46 | 0.56 | 0.49 | 0.58 |
| 8 | — | | 45.11 | 38.28 | >50.00 |
| 9 | 60.90 | 53.7 | 45.1 | | |
| 12 | — | | 34.77 | 49.17 | >50.00 |
| 13 | 26.10 | | >50.00 | >50.00 | >50.00 |
| 14 | 49.60 | | >50.00 | >50.00 | >50.00 |
| 15 | 5.70 | | 7.37 | 4.70 | 10.46 |
| 16 | 33.50 | | 44.88 | 36.73 | >50.00 |
| 17 | 14.10 | | 21.88 | 17.02 | 28.96 |
| 18 | 13.10 | | 14.45 | 16.72 | 37.21 |
| 19 | 0.13 | | 0.29 | 0.20 | 0.29 |
| 20 | 3.60 | | 25.54 | 6.61 | >50.00 |
| 21 | 0.90 | | 5.83 | 2.58 | 7.52 |
| 22 | 12.80 | | >50.00 | 28.55 | >50.00 |
| 23 | 9.00 | | 15.92 | 9.81 | 21.20 |
| 24 | 15.10 | | 34.40 | 24.06 | >50.00 |
| 25 | 0.67 | | 5.57 | 1.36 | 8.40 |
| 26 | 17.10 | | 20.76 | 21.68 | 48.03 |
| 27 | 2.10 | | 6.08 | 2.43 | 10.49 |
| 28 | 1.70 | | 5.47 | 3.59 | 14.94 |
| 29 | 0.53 | | 0.54 | 0.84 | 17.97 |
| 30 | 0.87 | | 5.67 | 1.57 | >50.00 |
| 31 | 33.50 | | 44.79 | 37.05 | >50.00 |
| 32 | 31.40 | | 34.27 | 34.30 | >50.00 |
| 33 | 1.80 | | 9.38 | 2.23 | 19.76 |
| 34 | 2.43 | | 17.63 | 20.74 | 33.28 |
| 35 | 2.22 | | 23.12 | 47.19 | >50.00 |
| 36 | — | | 0.83 | 0.51 | 0.57 |
| 37 | 2.60 | | 6.39 | 3.54 | >50.00 |
| 38 | 3.00 | | 17.03 | 48.40 | 47.35 |

Substituted β-carbolines and analog compounds 39 to 57 were tested for antiproliferative activity against HPAC, Mia-PaCa2 and Panc-1 pancreatic cancer cell lines and MCF-7 and MDA-MB-468 breast cancer cell lines. Table 2 lists the IC50 values for the substituted β-carbolines and analogs thereof. Compounds 42, 43, 44, 45, and 47 demonstrated significantly lower IC50 values.

TABLE 2

| Cmpd | HPAC IC50 (μM) | Mia-PaCa2 IC50 (μM) | Panc-1 IC50 (μM) | MCF-7 IC50 (μM) | MDA-MB-468 IC50 (μM) |
|---|---|---|---|---|---|
| 39 | 20.542 | 31.897 | 26.490 | >10 | >10 |
| 40 | — | | | 34.01 | 10.29 |
| 41 | 7.72 | 3.63 | >10 | >10 | >10 |
| 42 | 3.83 | 0.58 | 6.11 | 2.04 | 1.11 |
| 43 | 4.03 | 1.17 | 4.56 | 7.83 | 1.41 |
| 44 | 2.37 | 0.33 | 2.56 | 6.60 | 1.20 |
| 45 | 6.18 | 1.17 | 2.92 | 6.85 | 1.77 |
| 46 | >50 | 41.671 | >50 | >50 | >50 |
| 47 | 4.792 | 2.951 | >50 | 6.42 | 4.47 |
| 48 | 49.973 | 13.503 | >50 | 48.62 | 6.05 |
| 49 | >50 | 33.594 | >50 | >50 | 49.95 |

TABLE 2-continued

| Cmpd | HPAC IC50 (μM) | Mia-PaCa2 IC50 (μM) | Panc-1 IC50 (μM) | MCF-7 IC50 (μM) | MDA-MB-468 IC50 (μM) |
|---|---|---|---|---|---|
| 50 | >50 | >50 | >50 | >50 | 14.72 |
| 51 | >50 | 13.084 | >50 | 6.78 | 6.54 |
| 52 | 35.477 | 8.631 | >50 | 7.61 | 4.99 |
| 53 | 49.999 | 40.405 | >50 | >50 | 30.23 |
| 54 | 10.868 | 26.213 | 30.252 | 11.39 | 5.09 |
| 55 | 12.857 | 17.522 | 23.272 | 17.62 | 5.67 |
| 56 | 21.230 | 37.352 | 33.861 | 50.80 | 14.23 |
| 57 | 44.193 | 34.019 | 41.265 | 51.98 | 17.81 |

EXAMPLE 4

In vivo Breast and Prostate Cancer Models

Figure 2A:
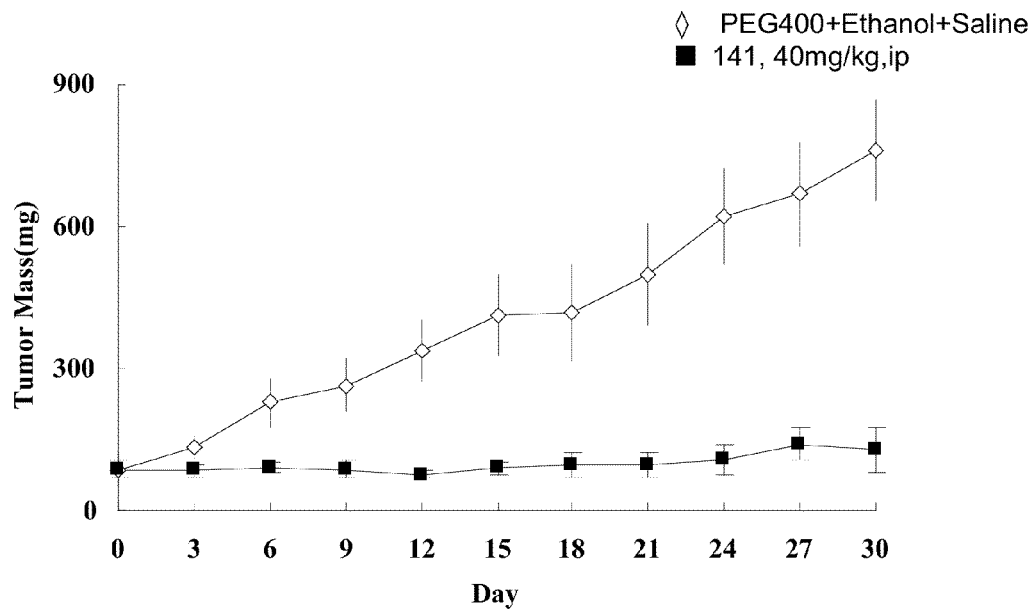
FIGS. 2A-2B illustrate antitumor activity on tumor mass (FIG. 2A) and on body weight (FIG. 2B) of compound 19 treatment in nude mice bearing human MDA-MB-468 breast cancer xenografts.
Figure 2B:
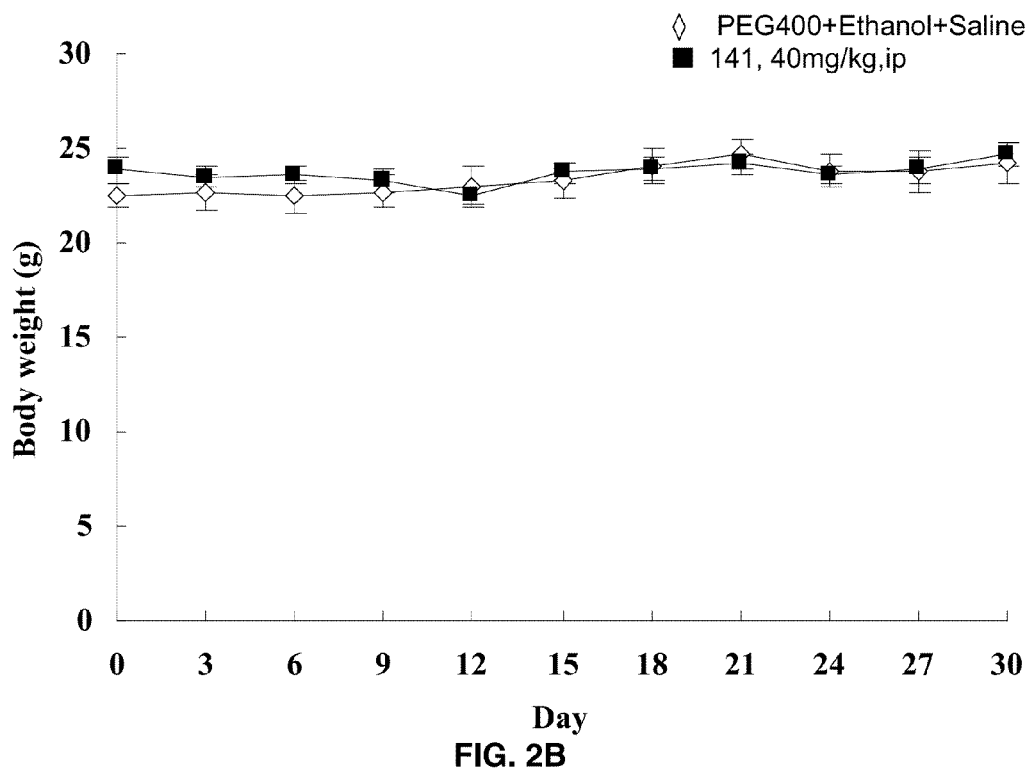
Figure 3A:
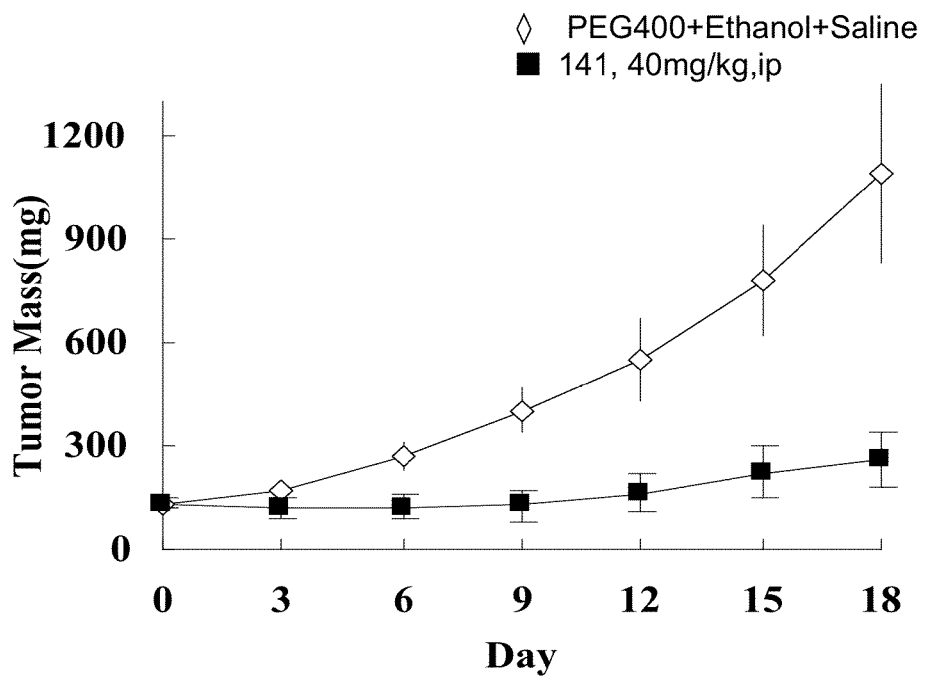
FIGS. 3A-3B illustrate antitumor activity on tumor mass (FIG. 3A) and on body weight (FIG. 3B) of compound 19 treatment in nude mice bearing Panc-1 human pancreatic cancer xenografts.
Figure 3B:
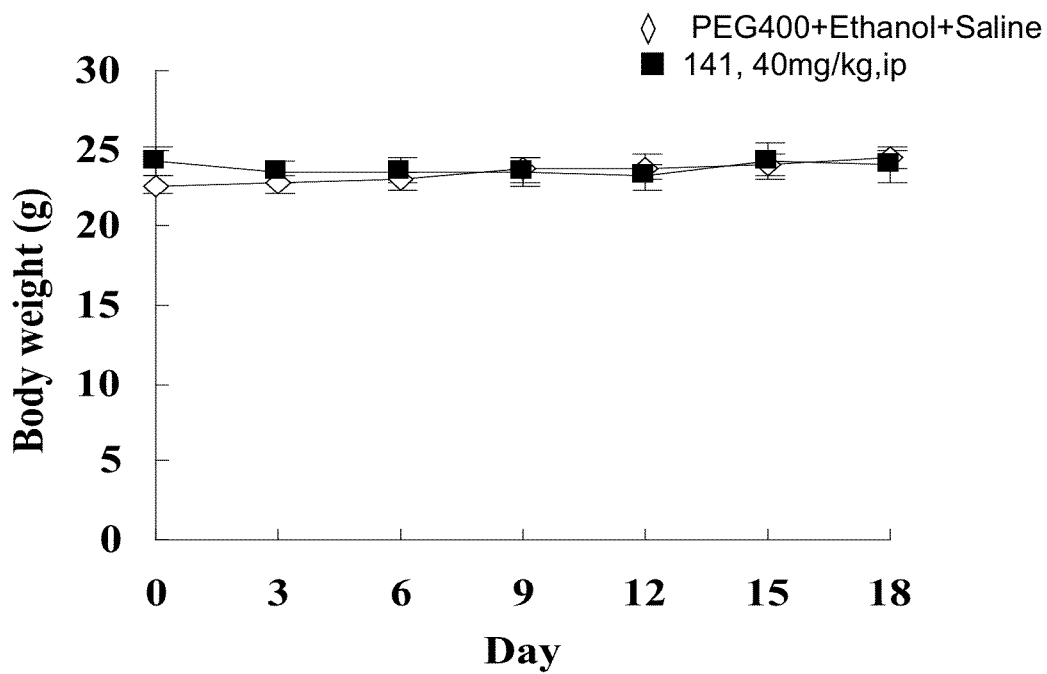

Nude mice bearing MDA-MB-468 breast cancer (FIGS. 2A-2B) and Panc-1 pancreatic cancer (FIGS. 3A-3B) xenografts were administered 40 mg/kg i.p. of compound 19 and tumor mass and body weights were measured daily for 18 days compared to a PEG-ethanol-saline control. After 18 days the tumor mass had not increased nor had body weight decreased in these mice.

Figure 4A:
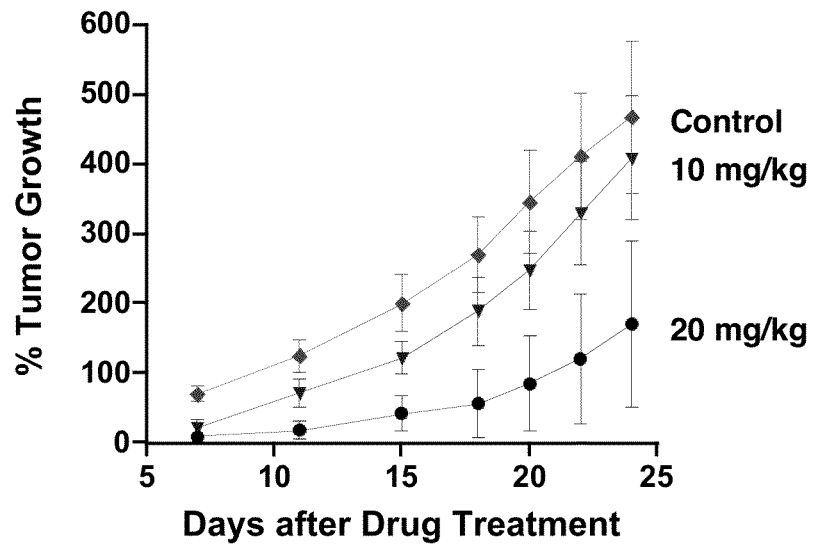
FIGS. 4A-4B illustrate antitumor activity on tumor growth (FIG. 4A) and on body weight (FIG. 4B) of compound 19 treatment in nude mice bearing human DUI145 prostate cancer xenografts.
Figure 4B:
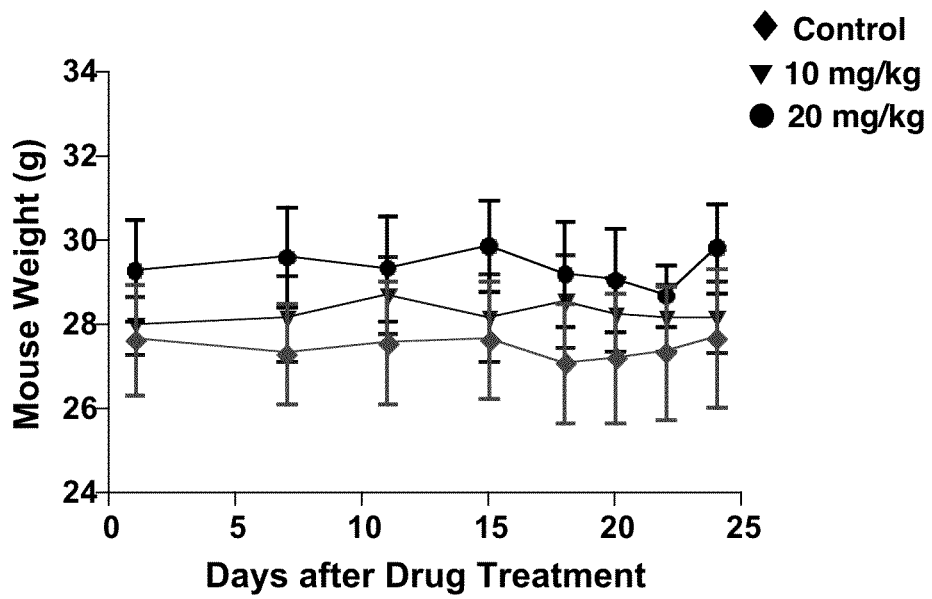

Nude mice bearing DU145 prostate cancer xenografts were administered i.p. 10 mg/kg, 20 mg/kg or control of compound 19 and tumor growth (FIG. 4A) and body weight (FIG. 4B) was monitored over 25 days. Although the percent of tumor growth at about day 7 in the presence of 10 mg/kg cmpd. 19 was less than control and substantially the same as with a dose of 20 mg/kg, the rate of tumor growth over the 25 days was about equivalent to that of control. A dose of 20 mg/kg showed significant decrease in tumor growth compared to 10 mg/kg and control. Body weights remained fairly constant for each dosing level although the average body weight for 20 mg/kg>10 mg/kg>control over the 25 days.

EXAMPLE 5

β-carboline Induced Apoptosis

Flow cytometry experiments were performed to show the effects of Compound 19, and anticancer drugs Adriamycin or Camptothecin treatment on the cell cycle kinetics of various human cells (FIGS. 8A-8I and 9A-9I), MCF-7 breast cancer cells (FIGS. 5A-5F), A549 lung cancer cells (FIGS. 7A-7I), LNCaP (FIGS. 10A-10I), DU145 (FIGS. 11A-11I) and PC-3 (FIGS. 12A-12I) prostate cancer cells, as well as cultured normal human fibroblasts (FIGS. 6A-6F). The compound or drugs were applied at a concentration of 15 mM in 0.1% DMSO as the vehicle, and cells incubated for the time point indicated in hours (hr). The control samples were treated with vehicle without compound or drug. Red histograms represent cells in the G1/G0 phase (histogram to the left) and cells in the G2/M phases (histogram to the right). The interval between the G1/G) and G2/M histograms is the S-phase of the cell cycle. The subG1/GO histograms (cyan colored) represent cells undergoing apoptosis (programmed cell death).

Adriamycin and Camptothecin were included to show that the mechanism of anticancer activity of compound 19 differed from those of these conventional anticancer drugs. Thus, whereas Adriamycin and Camptothecin kill cancer cells by a mechanism(s) involving primarily G1 phase arrest, compound 19 on the other hand kills cancer cells by a G2/M arrest mechanism(s). This also will make combination therapy of compound 19 with these drugs rationale since one will be targeting multiple mechanisms of cancer cell destruction. Also, the results with the normal human fibroblast cells show that Compound 19 has no significant perturbation of the cell cycle of normal human cells implying that it will be a selective anticancer agent that will mainly destroy cancer cells while sparing normal cells, a very attractive property for a cancer drug. This is unlike the conventional chemotherapy drugs Adriamycin and Camptothecin which did not show selectivity between the cancer cells and the normal (fibroblast) cells and perturbed their cell cycle kinetics equally well.

The following references are cited herein.
1. Cao et al. Current Medicinal Chemistry 14:479-500 (2007).
2. Song et al. Bioorganic & Medicinal Chemistry Letters 12:1129-1132.
3. Sunder-Plassman et al. Bioorg. Med. Chem. 13:6094-6111.
4. Liu et al. Biochem. Pharmacol. 70:287-299.
5. Frédérich et al. J Pharmacol Exp Ther, 304(3):1103-1110 (2003).

One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A substituted β-carboline compound having the structure:

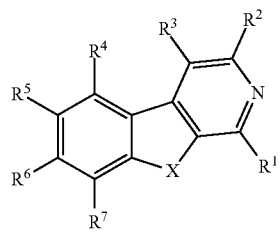

wherein X is NH or N—$C_1$-$C_4$ alkyl;
$R^1$ is 1-naphthyl, 1-naphthyl substituted with a halogen, 1-(1,2-dihydroacenaphthenyl), or 1-(1,2-dihydroacenaphthenyl) substituted with a halogen; and
$R^2$, $R^3$, $R^4$, $R^5$, $R^6$, and $R^7$ are independently H, OH, halogen, CN, $C_1$-$C_4$ alkoxy, $C_1$-$C_4$ haloalkoxy, C(O)O$C_1$-$C_4$ alkyl, ($C_1$-$C_4$)—$SO_2$—NH—($C_1$-$C_4$) alkyl, or phenyl;
wherein at least one of $R^2$, $R^3$, $R^4$, $R^5$, $R^6$, and $R^7$ is other than H and wherein, when $R^1$ is 1-naphthyl and one of $R^5$, $R^6$, or $R^7$ is $C_1$-$C_4$ alkoxy, then $R^2$, $R^3$, $R^4$, $R^5$, $R^6$, and $R^7$ are independently H, OH, halogen, CN, $C_1$-$C_4$ alkoxy, $C_1$-$C_4$ haloalkoxy, C(O)O$C_1$-$C_4$ alkyl, ($C_1$-$C_4$)—$SO_2$—NH—($C_1$-$C_4$) alkyl, or phenyl, and further wherein at least one of $R^2$, $R^3$, $R^4$, $R^5$, $R^6$, and $R^7$ is other than H.

2. The substituted β-carboline compound of claim 1, wherein X is NH;
$R^1$ is 1-naphthyl substituted with Br or F; and
$R^2$, $R^3$, $R^4$, $R^5$, $R^6$, and $R^7$ are independently H, OH, halogen, CN, $C_1$-$C_4$ alkoxy, $C_1$-$C_4$ haloalkoxy, —C(O)O$C_1$-$C_4$ alkyl, —($C_1$-$C_4$)—$SO_2$—NH—($C_1$-$C_4$) alkyl, or phenyl;
wherein at least one of $R^2$, $R^3$, $R^4$, $R^5$, $R^6$, and $R^7$ is other than H.

3. The substituted β-carboline compound of claim 1, wherein X is NH;
R$^1$ is 1-(1,2-dihydroacenaphthenyl) or 1(1,2-dihydroacenaphthenyl) substituted with Br or F; and
R$^2$, R$^3$, R$^4$, R$^5$, R$^6$, and R$^7$ are independently H, OH, halogen, CN, C$_1$-C$_4$ alkoxy, phenyl, C$_1$-C$_4$ haloalkoxy, —C(O)OC$_1$-C$_4$ alkyl, —(C$_1$-C$_4$)—SO$_2$—NH—(C$_1$-C$_4$) alkyl, or phenyl; wherein at least one of R$^2$, R$^3$, R$^4$, R$^5$, R$^6$, and R$^7$ is other than H.

4. The substituted β-carboline compound of claim 1, wherein X is N—CH$_3$;
R$^1$ is 1-(1,2-dihydroacenaphthenyl) or 1-(1,2-dihydroacenaphthenyl) substituted with Br or F; and
R$^2$, R$^3$, R$^4$, R$^5$, R$^6$, and R$^7$ are independently H, OH, halogen, CN, C$_1$-C$_4$ alkoxy, phenyl, C$_1$-C$_4$ haloalkoxy, —C(O)OC$_1$-C$_4$ alkyl, —(C$_1$-C$_4$)—SO$_2$—NH—(C$_1$-C$_4$) alkyl, or phenyl; wherein at least one of R$^2$, R$^3$, R$^4$, R$^5$, R$^6$, and R$^7$ is other than H.

5. A pharmaceutical composition comprising the substituted β-carboline compound of claim 1 and a pharmaceutically effective carrier.

6. A method for inhibiting cell proliferation in a mammal, comprising:
contacting the cells of said mammal with a therapeutically effective amount of one or more substituted β-carboline compounds of claim 1.

7. The method of claim 6, wherein the cells are breast cancer cells, colon cancer cells, prostate cancer cells, lung cancer cells, or pancreatic cancer cells.

8. A substituted β-carboline compound having the structure:

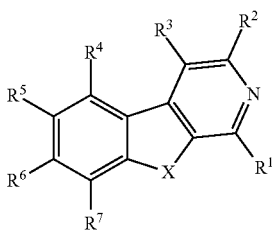

wherein X is NH or N—CH$_3$;
R$^1$ is 1-naphthyl, 1-naphthyl substituted with Br or F, 1-(1,2-dihydroacenaphthenyl) or 1-(1,2-dihydroacenaphthenyl) substituted with Br or F; and
R$^2$, R$^3$, R$^4$, R$^5$, R$^6$, and R$^7$ are independently H, OH, Br, Cl, CN, OCH$_3$, OCF$_3$, C(O)OCH$_2$CH$_3$, CH$_2$SO$_2$NHCH$_3$, or phenyl;
wherein at least one of R$^2$, R$^3$, R$^4$, R$^5$, R$^6$, and R$^7$ is other than H and wherein, when R$^1$ is 1-naphthyl and one of R$^5$, R$^6$, or R$^7$ is —OCH$_3$, then R$^2$, R$^3$, R$^4$, R$^5$, R$^6$, and R$^7$ are independently H, OH, Br, Cl, CN, OCF$_3$, C(O)OC$_1$-C$_4$ alkyl, (C$_1$-C$_4$)—SO$_2$—NH—(C$_1$-C$_4$) alkyl, or phenyl, and further wherein at least one of R$^2$, R$^3$, R$^4$, R$^5$, R$^6$, and R$^7$ is other than H.

9. The substituted β-carboline compound of claim 8, wherein X is NH; R$^1$ is 1-naphthyl; R$^2$ is H or C(O)OCH$_2$CH$_3$; R$^3$ is H or phenyl; R$^4$ is H; R$^5$ is H, OH, Cl, Br, CN, —OCF$_3$, or —CH$_2$SO$_2$NHCH$_3$; R$^6$ is H; and R$^7$ is H; wherein at least one of R$^2$, R$^3$, or R$^5$ is other than H.

10. The substituted β-carboline compound of claim 8, wherein X is NH; R$^1$ is 1-(5-fluoro-naphthyl) or 1-(5-bromo-naphthyl); R$^2$, R$^3$, R$^4$, R$^6$, and R$^7$ are H; and R$^5$ is OCH$_3$.

11. The substituted β-carboline compound of claim 8, wherein X is NH; R$^1$ is 1-(1,2-dihydroacenaphthenyl); R$^2$, R$^3$, R$^4$, R$^6$, and R$^7$ are H; and R$^5$ is OCH$_3$.

12. A pharmaceutical composition comprising the substituted β-carboline compound of claim 8 and a pharmaceutically effective carrier.

13. A β-carboline compound that is selected from the group consisting of:
1-(naphthalen-1-yl)-9H-pyrido[3,4-b]indol-6-ol,
6-methoxy-1-(naphthalen-1-yl)-4-phenyl-9H-pyrido[3,4-b]indole,
N-methyl-1-(1-(naphthalen-1-yl)-9H-pyrido[3,4-b]indol-6-yl)methane sulfonamide,
1-(5-fluoronaphthalen-1-yl)-6-methoxy-9H-pyrido[3,4-b]indole,
1-(5-bromonaphthalen-1-yl)-6-methoxy-9H-pyrido[3,4-b]indole,
1-(5-bromonaphthalen-1-yl)-6-methyl-9H-pyrido[3,4-b]indole,
1-(1,2-dihydroacenaphthalen-5-yl)-6-methoxy-9H-pyrido[3,4-b]indole,
1-(naphthalen-1-yl)-6-(trifluoromethoxy)-9H-pyrido[3,4-b]indole,
1-(naphthalen-1-yl)-9H-pyrido[3,4-b]indole-6-carbonitrile,
6-bromo-1-(naphthalen-1-yl)-9H-pyrido[3,4-b]indole,
ethyl-6-methoxy-1-(naphthalen-1-yl)-9H-pyrido[3,4-b]indole-3-carboxylate, and
9-methyl-1-(naphthalen-1-yl)-9H-pyrido[3,4-b]indole.

* * * * *